(12) United States Patent
Zeligs

(10) Patent No.: US 8,080,577 B2
(45) Date of Patent: Dec. 20, 2011

(54) DIINDOLYLMETHANE FORMULATIONS FOR THE TREATMENT OF LEIOMYOMAS

(75) Inventor: Michael A. Zeligs, Boulder, CO (US)

(73) Assignee: Bioresponse, L.L.C., Boulder, CO (US)

( * ) Notice: Subject to any disclaimer, the term of this patent is extended or adjusted under 35 U.S.C. 154(b) by 1648 days.

(21) Appl. No.: 11/124,571

(22) Filed: May 6, 2005

(65) Prior Publication Data

US 2005/0267193 A1 Dec. 1, 2005

Related U.S. Application Data

(60) Provisional application No. 60/569,478, filed on May 6, 2004.

(51) Int. Cl.
- A61K 31/405 (2006.01)
- A61K 31/40 (2006.01)
- A61K 31/535 (2006.01)
- A61K 31/335 (2006.01)
- A61K 31/35 (2006.01)
- A61K 31/05 (2006.01)

(52) U.S. Cl. ..... 514/415; 514/414; 514/418; 514/234.5; 514/452; 514/456; 514/733

(58) Field of Classification Search .......... 514/415, 514/414, 418, 234.5
See application file for complete search history.

(56) References Cited

U.S. PATENT DOCUMENTS

| | | | |
|---|---|---|---|
| 5,635,215 A | 6/1997 | Boschetti et al. | |
| 5,718,921 A | 2/1998 | Mahtiowitz et al. | |
| 5,770,599 A * | 6/1998 | Gibson | 514/228.2 |
| 5,830,887 A | 11/1998 | Kelly | |
| 5,895,787 A | 4/1999 | Arffmann et al. | |
| 5,948,808 A | 9/1999 | Safe | |
| 6,086,915 A | 7/2000 | Zeligs et al. | |
| 6,399,645 B1 | 6/2002 | Bell et al. | |
| 6,477,229 B1 | 11/2002 | Grosser | |
| 6,534,085 B1 | 3/2003 | Zeligs | |
| 6,613,792 B1 | 9/2003 | Ellenberger et al. | |
| 6,656,963 B2 | 12/2003 | Firestone et al. | |
| 6,689,387 B1 | 2/2004 | Zeligs | |
| 6,800,655 B2 | 10/2004 | Jong et al. | |
| 7,348,352 B2 | 3/2008 | Zeligs | |
| 7,384,971 B2 | 6/2008 | Zeligs | |
| 7,384,972 B2 | 6/2008 | Zeligs | |
| 2001/0002393 A1 | 5/2001 | Palmer et al. | |
| 2002/0115708 A1 | 8/2002 | Safe | |

(Continued)

FOREIGN PATENT DOCUMENTS

EP 0566226 10/1993
(Continued)

OTHER PUBLICATIONS

De Leo et al. "A Benefit-Risk Assessment of medical treatment of uterine leiomyomas," Drug Safety, 2002, vol. 25, No. 11, pp. 760-779.*

(Continued)

Primary Examiner — Shengjun Wang
(74) Attorney, Agent, or Firm — Jones Day

(57) ABSTRACT

The present invention relates to compositions and methods for treating or preventing leiomyomas by administration of diindolylmethane and diindolylmethane-related indoles. The present invention also relates to compositions and methods for treating or preventing leiomyomas by administration of diindolylmethane in combination with an EGFR antagonist. The methods provide non-invasive treatments for leiomyomas.

14 Claims, 1 Drawing Sheet

U.S. PATENT DOCUMENTS

Figure 1A:
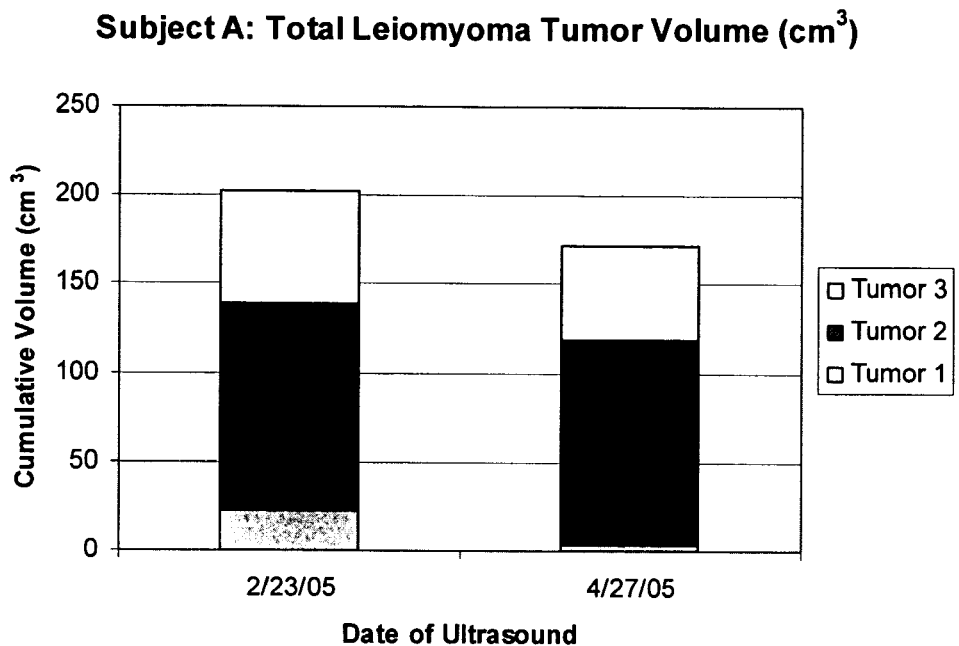

| | | | |
|---|---|---|---|
| 2002/0147155 | A1 | 10/2002 | Foster et al. |
| 2003/0096855 | A1 | 5/2003 | Zeligs |
| 2003/0211165 | A1 | 11/2003 | Vogel |
| 2003/0220377 | A1 | 11/2003 | Chesworth |
| 2003/0223956 | A1 | 12/2003 | Goupil et al. |
| 2004/0043965 | A1 | 3/2004 | Jong et al. |
| 2004/0072891 | A1 | 4/2004 | Zeligs |
| 2004/0156910 | A1 | 8/2004 | Zeligs |

FOREIGN PATENT DOCUMENTS

| | | |
|---|---|---|
| WO | WO 96/30347 | 3/1996 |
| WO | WO 96/33980 | 10/1996 |
| WO | WO 97/02266 | 1/1997 |
| WO | WO 97/30034 | 8/1997 |
| WO | WO 97/38983 | 10/1997 |
| WO | WO 99/55683 | 11/1999 |
| WO | WO 00/31048 | 6/2000 |
| WO | WO 01/20990 | 3/2001 |

OTHER PUBLICATIONS

Akkar et al., 2003, "Formulation of intravenous carbamazepine emulsions by SolEmuls technology," Eur J. Pharm Biopharm., vol. 55:305-12.

Alberts, B et al., Molecular Biology of the Cell 2$^{nd}$ ed., 1989, Garland Publishing, Inc., New York, pp. 1193-1194, 1204-1206.

Anjun et al., 1988, "Spontaneous occurrence and experimental induction of leiomyoma of the ventral ligament of the oviduct of the hen," Res Vet Sci., vol. 45:341-8.

Arbeit, et al., "Chronic estrogen-induced cervical and vaginal squamous carcinogenesis in human papillomavirus type 16 transgenic mice", Apr. 1996, Proc Natl Acad Sci, USA 93:2930-2935.

Arici et al., 2003, "Expression, menstrual cycle-dependent activation, and bimodal mitogenic effect of transforming growth factor-beta1 in human myometrium and leiomyoma," Am J Obstet Gynecol., vol. 188(1):76-83.

Auborn et al., 2000, "Treatment of Human Papillomavirus Gynecologic Infections", Clin Lab Med 20:407-22.

Auborn KJ., 2002, "Therapy for recurrent respiratory papillomatosis," Antiviral Therapy, MTM Publications, London GB., vol. 7(1):1-9.

Baugh SM et al., "Treatment of cervical dysplasia with indole-3-carbinol" in The Ray A. Barlow Scientific Symposium, Jan. 23, 1998, Shreveport : The Center for Excellence in Cancer Research, Treatment and Education, Louisiana State University Medical Center, Shreveport (LA), p. 3.

Bell, MC et al., "Placebo-controlled Trial of Indole-3-Carbinol in the Treatment of Cervical Dysplasia", Abstracts Presented for the Thirtieth Annual Meeting of the Society of Gynecologic Oncologists Mar. 1999, Gynecol. Oncol. 72, 443-527 (Abstract 13).

Bell, MC et al., "Placebo-Controlled Trial of Indole-3-Carbinol in the Treatment of CIN", 2000, Gynecologic Oncology, 78:123-129.

Berto et al., 2003, "A comparative analysis of structure and spatial distribution of decorin in human leiomyoma and normal myometrium," Biochim Biophys Acta., vol. 1619:98-112.

Bioresponse Letter, Dec. 29, 1998.

Bioresponse-DIM Indolplex Product Information Brochure, Dec. 15, 1998.

Bjeldanes et al., 1991, "Aromatic hydrocarbon responsiveness-receptor agonists generated from indole-3-carbinol in vitro and in vivo: comparisons with 2,3,7,8,-tetrachlorodibenzo-p-dioxin," Proc. Natl. Acad. Sci. USA 88:9543-9547.

Bradfield et al., "High-performance liquid chromatographic analysis of anticarcinogenic indoles in *Brassica oleracea*", 1987, J Agric Food Chem 35:46-49.

Bradfield et al., 1987, "Structure- Activity relationships of dietary indoles: a proposed mechanism of action as modifiers of xenobiotic metabolism," J Toxicol Environ Health, vol. 21:311-23.

Bradlow et al. "Multifunctional aspects of the action of indole-3-carbinol as an anyi-tumor agent," Annals of New York Academy of Sciences, 1999, vol. 889, pp. 204-213.

Bradlow et al., "2-hydroxyestrone: the 'good' estrogen", 1996, J Endocrin 150:S259-S265.

Brandi et al., 2003, "A new indole-3-carbinol tetrameric derivative inhibits cyclin-dependent kinase 6 expression, and induces G1 cell cycle arrest in both estrogen-dependent and estrogen-independent breast cancer cell lines," Cancer Res., vol. 63(14):4028-36.

Buchwald et al., 1980, "Long-term, continuous intravenous heparin administration by an implantable infusion pump in ambulatory patients with recurrent venous thrombos," Surgery, vol. 88:507-16.

Cancer Medicine 3rd edition, 1993, JF Holland ed., Lea & Febiger, Malvern, PA p. 1633.

Chang et al., 1999, "Cytostatic and antiestrogenic effects of 2-(Indo1-3-ylmethyl)-3,3'-diindolylmethane, a major in vivo product of dietary indole-3-carbinol," Biochem. Pharmacol. 58:825-834.

Chapman et al., 2004, "Expression and deoxyribonucleic acid-binding activity of the nuclear factor kappaB family in the human myomertrium during pregnancy and labor," J Clin Endocrinol Metab., vol. 89:5683-93.

Chen et al., "Aryl hydrocarbon receptor-mediated antiestrogenic and antitumorigenic activity of diindoylmethane", 1998, Carcinogenesis 19:1631-1639.

Chen et al., 2001, "Indole-3-carbinol and diindolylmethane induce apoptosis of human cervical cancer cells and in murine HPV16-transgenic preneoplastic cervical epithelium," J Nutr., vol. 131:3294-302.

Dashwood, R.H., 1998, "Indole-3-carbinol: anticarcinogen or tumor promoter in brassica vegetables?" Chem Biol. Interact., 110(1-2):1-5.

de Kruif et al., 1991, ". Structure elucidation of acid reaction products of indole-3-carbinol: detection in vivo and enzyme induction in vitro," Chem Biol Interact., vol. 80:803-15.

de Vet et al., 1994, "The role of cigarette smoking in the etiology of cervical dysplasia," Epidemiology 5:631-633.

During et al., 1989, "Controlled release of dopamine from a polymeric brain implant: in vivo characterization," Ann Neurol., vol. 25:351-56.

Exon, et al., 2000, "Dietary indole-3-carbinol alters immune functions in rats," J. Toxicol. Environ. Health A., 59(4):271-9.

Farman, 1975, "Benign smooth muscle tumors," S. Afr. Med. J., vol. 19:1333-40.

Flake et al., 2003, "Etiology and pathogenesis of uterine leiomyomas: a review," Environ Health Perspect. vol. 111:1037-54.

Flierman et al., 2005, "Rapid reduction of leiomyoma volume during treatment with the GnRH antagonist ganirelix," BJOG., vol. 112:638-42.

Foster et al., 1989, "Influence of selection for increased body weight on the incidence of leiomyomas and leiomyosarcomas in Japanese quail," Poult Sci., vol. 68:1447-53.

Gao et al., 2002, "Endocrine disruption by indole-3-carbinol and tamoxifen: blockage of ovulation," Toxicol Appl Pharmacol., vol. 183:179-88.

Gillner et al., 1985, "Interactions of indoles with specific binding sites for 2,3,7,8-tetrachlorodibenzo-p-dioxin in rat liver," Mol Pharmacol 28:357-363.

Gooptu et al., 2000, "Treatment of viral warts with cimetidine: and open-label study," Clin. Exp. Dermatol. 25(3):183-5.

Green et al., 2000, "Pathogenesis and treatment of juvenile onset recurrent respiratory papillomatosis," Oto-Laryngologic Clinics of North America, W.B. Saunders, Philadelphia, US., vol. 33(1):187-207.

Greenblatt et al., "Clinical studies with an anti-gonadotropin -danazol", 1971, Fertil Steril 22:102-112.

Hardman, et al. "Goodman & Gilman's The Pharmacological Basis of Therapeutics" (9$^{th}$ ed, 1996) pp. 51 and 57-58.

Harrison-Woolrych et al., 1994, "Quantification of messenger ribonucleic acid for epidermal growth factor in human myometrium and leiomyomata using reverse transcriptase polymerase chain reaction," J Clin Endocrinol Metab., vol. 78:1179-84.

Ho et al., "Urinary 2/16alpha-hydroestrone ratio: correlation with serum insulin-like growth factor binding protein-3 and a potential biomarker of breast cancer risk", 1998, Ann Acad Med Singapore 27:294-9.

Hong et al., 2002, "Bcl-2 family-mediated apoptotic effects of 3,3'-diindolylmethane (DIM) in human breast cancer cells," Biochem Pharmacol., vol. 63:1085-97.

Horiuchi et al., 2000, "HCG promotes proliferation of uterine leiomyomal cells more strongly than that of myometrial smooth muscle cells in vitro.," Mol Hum Reprod., vol. 6:523-8.

Howard et al., 1989, "Intracerebral drug delivery in rats with lesion-induced memory deficits," J Neurosurg., vol. 71:105-12.

Janmaat et al., 2003, "Small-molecule epidermal growth factor receptor tyrosine kinase inhibitors," Oncologist, vol. 8:576-86.

Janmaat et al., 2003, "The epidermal growth factor receptor pathway and its inhibition as anticancer therapy," Drugs Today (Barc) 39 Suppl C:61-80.

Jin et al., "Indole-3-carbinol prevents cervical cancer in human papillomavirus type 16 (HPV16) transgenic mice, 1999, Cancer Res 59"3991-7.

Komura et al., "Catecholestrogen as a natural antioxidant", 1996, Ann NY Acad Sci 786:419-29.

Langer et al., New methods of drug delivery, Science, vol. 249:1527-1533.

Larsen-Su et al., 2001, "Transplacental exposure to indole-3-carbinol induces sex-specific expression of CYP1A1 and CYP1B1 in the liver of Fischer 344 neonatal rats," Toxicological Sci. 64:162-168.

Lee et al., 2004, "Inhibitory effects of Scutellaria barbata D. Don on human uterine leiomyomal smooth muscle cell proliferation through cell cycle analysis," Int Immunopharmacol., vol. 4:447-54.

Lefebvre et al., 2002, "Clinical Practice Gynaecology Committee, Society for Obstetricians and Gynaecologists of Canada. The management of uterine leiomyomas," J Obstet Cynaecol Can., vol. 25:396-418.

Leong et al., 2004, "Potent ligand-independent estrogen receptor activation by 3,3'-diindolylmethane is mediated by cross talk between the protein kinase A and mitogen-activated protein kinase signaling pathways," Mol Endocrinol., vol. 18:291-302.

Levy et al., 1985, "Inhibition of calcification of bioprosthetic heart valves by local controlled-release diphosphonate," Science, vol. 228:190-192.

Liehr et al., 1995, "4-Hydroxylation of estradiol by human uterine myometrium and myoma microsomes: implications for the mechanism of uterine tumorigenesis," Proc Natl Acad Sci USA., vol. 92:9220-4.

Liu et al., 1994, "Indolo[3,2-b]carbozole: a dietary-derived factor that exhibits both antiestrogenic and estrogenic activity," J. Natl. Cancer Inst. 86:1758-1765.

Loria RM et al., 1990, "Immune response facilitation and resistance to virus and bacterial infectionis with dehydroepiandrosterone (DHEA)," Biologic Role of Dehydroepiandrosterone, pp. 107-130.

Loub et al., 1975, "Aryl hydrocarbon hydroxylase induction in rat tissues by naturally occurring indoles of cruciferous plants," J. Natl. Cancer Inst. 54:985-988.

Marshall et al., 1997, "Variation in the incidence of uterine leiomyoma among premenopausal women by age and race," Obstet Gynnecol., vol. 90:967-73.

Michnovicz et al., 1986, "Increased 2-hydroxylation of estradiol as a possible mechanism for the anti-estorgenic effect of cigarette smoking," N Engl J Med 315:1305-1309.

Michnovicz et al., 1988, "Increased urinary catechol estrogen excretion in female smokers," Steroids 52:69-83.

Michnovicz et al., 1991, "Cimetidine inhibits catechol estrogen metabolism in women," Metabolism, 40(2):170-74.

Michnovicz et al., 1997, "Changes in levels of urinary estrogen metabolites after oral indole-3-carbinol treatment in humans", J Natl Cancer Inst 89:718-23.

Morfin R et al., 1994, "Pregnenolone and dehydroepiandrosterone as precursors of native 7-hydroxylated metabolites which increase the immune response in mice," J of Steroid Biochemistry and Molecular Biology, Elsevier Science Ltd., Oxford, GB, vol. 50(1/2) Jul. 1994, pp. 91-100.

Muzandu et al., 2005, "Lycopene and beta-carotene ameliorate catechol estrogen-mediated DNA damage," Jpn J Vet Res., vol. 52:173-84.

Nair, 2003, "Contemporary management of fibroids," Ann Acad Med Singapore, Ann Acad Med Singapore, vol. 32:615-23.

Ponten and Guo, 1998, "Precancer of the Human Cervix", Cancer Surveys 32:201-229.

Langer and Peppas, 1983, "Chemical and physical structure of Polymers as carriers sfor controlled release of bioactive agents: a review," J. Macromol Sci Rec Macromol., Chem, vol. 23:61-126.

Rein, 2000, "Advances in uterine leiomyoma research: the progesterone hypothesis," Environ Health Perspect., 108 Suppl 5:791-3.

Riby et al., 2000, "Ligand-independent activation of estrogen receptor function by 3,3'-diindolylmethane in human breast cancer cells," Biochem. Pharmacol. 60:167-177.

Ritter et al., 2001, "Oxidations of 17beta-estradiol and estrone and their interconversions catalyzed by liver, mammary gland and mammary tumor after acute and chronic treatment of rats with indole-3-carbinol or beta-naphthoflavine," Can. J. Physiol. Pharmacol. 79(6):519-32.

Rosen et al., "Preliminary results of the use of indole-3-carbinol for recurrent respiratory papillomatosis", 1998, Otolaryngol Head Neck Surg 118:810-5.

Sah et al., 2004, "Epigallocatechin-3-gallate inhibits epidermal growth factor receptor signaling pathway. Evidence for direct inhibition of ERK1/2 and AKT kinases," J Biol Chem., vol. 279:12755-62.

Sahin et al., 2004, "Lycopene supplementation prevents the development of spontaneous smooth muscle tumors of the oviduct in Japanese quail," Nutr Cancer, vol. 50:181-9.

Saudek et al., 1989, "A preliminary trial of the programmable implantable medication system for insulin delivery," New Engl. J. Med., vol. 321:574-79.

Schneider et al., "Abnormal oxidative metabolism of estradiol in women with breast cancer", 1982, Proc Natl Acad Sci USA 79:3047-52.

Schwartz et al., 1995, "Cancer prevention with dehydroepiandrosterone and non-androgenic structural analogs," Journal of Cellular Biochemistry, 58/Suppl. 22, 210-217.

Schwartz et al., 1998, "Use of transvaginal ultrasonography to monitor the effects of tamoxifen on uterine leiomyoma size and ovarian cyst formation," J Ultrasound Med., vol. 17:699-703.

Sefton, 1987, "Implantable pumps," CRC Crit Ref., Biomed Eng., vol. 14:201.

Sepkovic et al., 2002, "Quantitative Determination of 3,3'-Diindolymethane in the urine of individuals receiving indole-3-carbinol," Nutr Cancer. 2001;41(1-2):57-63.

Sharma et al., 2001, "Inhibitory effect of silibinin on ligand binding to erbB1 and associated mitogenic signaling, growth, and DNA synthesis in advanced human prostate carcinoma cells," Mol Carcinog., vol. 30:224-36.

Shilling et al., 2001, "3,3'-diindolylmethane, a major condensation product of indole-3-carbinol, is a potent estrogen in the rainbow trout," Toxicology and Applied Pharmacology 170:191-200.

Smail et al., 1999, "Tyrosine kinase inhibitors. 15. 4-(Phenylamino)quinazoline and 4-(phenylamino)pyrido[d]pyrimidine acrylamides as irreversible inhibitors of the ATP binding site of the epidermal growth factor receptor," J Med Chem., vol. 42:1803-1815.

Spies et al., 2002, "Complications after uterine artery embolization for leiomyomas," Obstet Gynecol., vol. 100:873-80.

Stewart et al., 2004, "Resveratrol antagonizes EGFR-dependent Erk1/2 activation in human androgen-independent prostate cancer cells with associated isozyme-selective PKC alpha inhibition," Invest. New Drugs, vol. 22:107-117.

Stresser et al., 1995, "Mechanisms of tumor modulation by indole-3-carbinol: disposition and excretion in male fisher 344 rats," Drug Metabolism and Disposition 23:965-975.

Stresser et al., 1995, "The anticarcinogen 3,3'-Diindolyl-methane is an inhibitor of cytochrome P-450," J. Biochem. Toxicol., 10(4):191-201.

Strobelt et al., 1994, "Natural history of uterine leiomyomas in pregnancy," J Ultrasound Med., vol. 13:399-401.

Telimaa et al., "Placebo-controlled comparison of danazol and high-dose medroxyprogesterone acetate in the treatment of endometriosis", 1987, Gynecol Endocrinol 1:13-23.

Thomas et al., 1987, "Impact of gestrinone on the course of asymptomatic endometriosis" Br Med J 294:272.-74.

Tse et al., 1987, "Disposition of alpha-[(dimethylamino)methyl]-2-(3-ethyl-5-methyl-4-isoxazolyl)-1H-indole-3-methanol (59-801), a hypoglycaemic agent in rats, dogs and monkeys," Xenobiotica, 17(6):741-9.

Tzingounis et al., 1997, "Modern approach to endometriosis," Annals New York Acad Sci 816:320-330.

Venkatachalam et al., 2004, "Medical management of uterine fibroids with medroxyprogesterone acetate (Depo Provera): a pilot study," J Obstet Gynaecol., vol. 24:798-800.

Walboomers et al., 1999, "Human papillomavirus is a necessary cause of invasive cervical cancer worldwide," J. Pathol. 189:12-19.

Woodburn et al, 1999, "The epidermal growth factor receptor and its inhibition in cancer," Pharmacol. Ther., vol. 82:241-250.

Xu et al., 2002, "Stable isotope dilution high-performance liquid chromatography-electrospray ionization mass spectrometry method for endogenous 2- and 4-hydroxyestrones in human urine," J Chromatogr B Analyt Technol Biomed Life Sci., vol. 780:315-30.

Yuan F et al., "Prevention of Papillomavirus initiated cancer by the phytochemical Indole-3-Carbinol", Proceedings of the 17th International Papillomavirus Conference, Jan. 9-15, 1999 p. 73.

Zeligs et al., 2002, "Absorption-enhanced 3,3-dindolylmethane: human use in HPV-related, benign and pre-cancerous conditions," Proceedings of the Annual Meeting of the American Association for Cancer Research, New York, NY vol. 43, Mar. 2003, pp. 664, Abstract 3198.

Zeligs MA, "Diet and Estrogen Status: The Cruciferous Connection", 1998, J Med Food, 1:67-82.

Palomba et al., 2002, "Raloxifene Administration in Premenopausal Women with Uterine Leiomyomas: A Pilot Study", J. of Clinical Endocrinology & Metabolism 87 (8):3603-3608.

Plu-Bureau et al., 1994, "Progestogen use and decreased risk of breast cancer in a cohort study of premenopausal women with benign breast disease", Br. J. Cancer 70:270-277.

Sanderson et al., 2001, "2,3,7,8-Tetrachlorodibenzo-$p$-dioxin and Diindolylmethanes Differentially Induce Cytochrome P450 1A1, 1B1, and 19 in H295R Human Adrenocortical Carcinoma Cells", Toxicological Sciences 61:40-48.

* cited by examiner

DIINDOLYLMETHANE FORMULATIONS FOR THE TREATMENT OF LEIOMYOMAS

This application claims priority to U.S. Provisional Application No. 60/569,478, filed on May 6, 2004, which is incorporated herein by reference in its entirety.

1. FIELD OF THE INVENTION

The present invention relates to compositions and methods for treating or preventing leiomyomas by administration of diindolylmethane or a diindolylmethane-related indole. The present invention also relates to compositions and methods for treating or preventing leiomyomas by administration of diindolylmethane or a diindolylmethane-related indole in combination with an EGFR antagonist. The methods provide non-invasive treatments for leiomyomas.

2. BACKGROUND OF THE INVENTION

2.1. Clinical Importance of Uterine Leiomyomas

Leiomyomas are benign soft-tissue tumors that arise from smooth muscle tissue. Leiomyomas of the uterus are the most common, abnormal pelvic growth diagnosed in women. Leiomyomas are also called "myomas" and "uterine fibroids". As benign, non-cancerous, growths arising from uterine smooth muscle (myometrium), leiomyomas are unrelated to the common forms of uterine cancer and uterine cervical cancer which typically arise from the uterine lining (endometrium) or cervical epithelium, respectively. In the United States, leiomyomas occur in the majority of all women (Flake et al., 2003, Environ Health Perspect. 111:1037-54). Leiomyomas are particularly prevalent in African-American women, who report a 3 times greater rate of occurrence than Caucasian women (Marshall et al., 1997, Obstet. Gynecol. 90:967-73). Although rare, leiomyomas also develop outside the uterus in both women and men. Extra-uterine sites of leiomyoma occurrence include the nipple, esophagus, scrotum, and seminal vesicles which all possess smooth muscle (Farman, 1975, S Afr Med J. 49:1333-40). In addition, rare, familial syndromes, including diffuse leiomyomatosis and Alport Syndrome, are associated with recurrent leiomyomas in multiple anatomic sites. Smooth muscle tumors are also common in the avian species, typically involving the oviduct, an analogous structure to the mammalian uterus. Japanese quail (*Coturnix cturnix japonica*) and the common chicken hen (*Gallus domesticus*) are especially affected, with prevalences varying up to 60% (Foster et al., 1989, Poult Sci. 68:1447-53; and Anjum et al., 1988, Res Vet Sci. 45:341-8). Despite their frequency, the pathobiology of leiomyomas remains poorly understood.

In women, leiomyomas contribute to a spectrum of symptoms including heavy, irregular, and prolonged menstrual bleeding and anemia. Leiomyomas may also cause pelvic discomfort, and bowel and bladder dysfunction from pressure on these adjacent structures. Leiomyomas have also been associated with infertility and recurrent abortion. The presence of leiomyomas can interfere with normal labor during the birth process, necessitating cesarean section. In addition to abnormal labor, leiomyomas restrict normal intra-uterine growth and predispose to postpartum hemorrhage secondary to uterine atony.

Histologically, leiomyomas arise from smooth muscle, show benign cell structure, and are distinct and unrelated to precancerous and cancerous cell growth affecting the uterine lining or endometrium. Leiomyomas arise from genetically similar clones of uterine smooth muscle cells, and they grow under the influence of local growth factors and in the presence of sex hormones. Evidence supports a more important contribution of progesterone than estrogen to myoma growth (Rein, 2000, Environ Health Perspect. 108 Suppl 5:791-3). The contribution of progesterone and estrogen to leiomyoma growth is uncertain, however, based on the observation that leiomyomas often recede in size during pregnancy, which is a time of high circulating estrogen and progesterone levels (Strobelt et al., 1994, J Ultrasound Med. 13:399-401). Adding to the uncertainty of the role of estrogen in myoma etiology, the clinical use of tamoxifen, an estrogen antagonist drug, has been associated with increased, not decreased, growth of leiomyomas (Schwartz et al., 1998, J Ultrasound Med. 17:699-703). Typically, leiomyomas in women appear after menarche, proliferate and grow during the reproductive years, and stabilize or regress after menopause. The diagnosis of leiomyomas is based on patient signs and symptoms, followed by physical and pelvic examination, demonstrating a pelvic mass, and confirmation by trans-abdominal or trans-vaginal ultrasonic visualization. The etiology and hormonal contributions to leiomyomas remain poorly understood.

Study of the biochemistry of uterine leiomyomas has shown that myoma tissue preferentially metabolizes estrogen to 4-hydroxy estrogen metabolites, demonstrating a different pattern of estrogen metabolism than surrounding normal myometrial smooth muscle (Liehr et al., 1995, Proc Natl Acad Sci USA 92:9220-4). Biochemical comparison of the extra-cellular matrix of leiomyoma tissue compared to surrounding normal tissue reveals differences in the composition and structure of collagen which may contribute to abnormal growth (Berto et al., 2003, Biochim Biophys Acta. 1619:98-112.)

Other than surgery, there are few safe and effective treatment options available to women with symptomatic leiomyomas. Gonadotropin-releasing hormone agonists (GnRH-a) inhibit steroidogenesis and induce pharmacologic menopause. Through this mechanism, GnRH-a's can reduce leiomyoma volume by 50% in 3 to 6 months. However, because these agents cause severe menopausal symptoms and the risk of estrogen-deficiency related bone loss (osteoporosis), these drugs cannot be used for prolonged periods of time. Moreover, leiomyomas tend to regrow after cessation of GnRH-a therapy. As a result, GnRH-a treatment, independent of subsequent surgery, is not recognized as an effective, long-term treatment of leiomyomas.

The surgical procedures for treatment of uterine leiomyomas are myomectomy and hysterectomy (Nair, 2003, Ann Acad Med. Singapore. 32:615-23). Myomectomy, done either through a laparotomy or laparoscopy, is performed to remove the leiomyoma and conserve the uterus. This is usually attempted in young women who may desire future pregnancy. Unfortunately, myomectomy is followed by extensive pelvic adhesions that themselves can reduce future fertility. Additionally, if the leiomyoma penetrates the uterine cavity, any future pregnancy after myomectomy carries an increased risk of uterine rupture and delivery has to be accomplished by cesarean section.

Hysterectomy remains the definitive surgical treatment for leiomyomas. Symptomatic uterine leiomyomas account for approximately one third of all hysterectomies performed among middle-aged women (Nair, 2003, Ann Acad Med. Singapore. 32:615-23). The impact of this surgical approach to leiomyomas is extremely costly considering the long postoperative time and recuperation away from work. There are also well known complications to hysterectomy. These complications include postoperative hemorrhage, fever, or injury to adjacent organs.

Two recent modalities have been developed for less extreme interventional treatment of uterine fibroids: myolysis and uterine artery embolization (Lefebvre et al., 2003, J Obstet Gynaecol Can. 25:396-418). Myolysis refers to the technique of disrupting or abolishing the blood supply to the fibroid causing shrinkage by using bipolar or monopolar electrosurgery. It is only applicable if there are less than three fibroids present and/or the largest one measures less than 10 cm in diameter. The procedure is also not recommended for women who wish to get pregnant, since the risk of uterine rupture is high. Uterine artery embolization (UAE) is a procedure done by radiologists with the objective of eliminating the blood supply to leiomyoma tissue. After some months following the treatment, UAE typically results in an average reduction of myoma tissue volume of about 50%. However, acutely causing the death of myoma tissue due to arterial blockage has side effects. The procedure can be followed by severe pain requiring hospitalization. Some concern about future fertility has been raised following UAE, as well as lack of ability to treat all leiomyomas present. A portion of women undergoing uterine artery embolism develop subsequent amenorrhea and menopause due to inadvertent impairment of ovarian function (Spies et al., 2002, Obstet. Gynecol. 100: 873-80).

For women with symptomatic leiomyomas, who wish to preserve fertility or avoid surgery, more conservative, more effective, and safer methods of medical treatment are needed. Ideally, improved medical treatments to manage leiomyomas will preserve an intact uterus, better preserve fertility, and, as adjunct treatments, improve the safety and long-term efficacy of more conservative treatment modalities such as UAE and laparoscopic myomectomy.

2.2. Biologic Activities of Cruciferous Indoles

Cruciferous vegetables contain a family of plant protective compounds called glucobrassicins which give rise to active compounds with the indole molecular ring, exemplified by indole-3-carbinol (I3C). However, I3C is highly unstable in water and acid. When given orally, I3C generates a number of gastric reaction products with a variety of biologic actions (De Kruif et al., 1991, Chem Biol Interact; 80:303-15). These products are highly enzyme inducing and associated with both the inactivation and activation of carcinogens. As such, the use of I3C has been associated with both the growth inhibition and growth promotion in experimental cancers. In addition, unwanted enzyme induction by I3C reaction products following oral I3C use may alter the metabolism of other drugs, steroid hormones including estrogen, and contraceptives raising safety concerns. Oral use of I3C in humans has been shown to increase production of the 4-hydroxy estrogen metabolites previously associated with leiomyoma tissue (Michnovicz et al., 1997, J Natl Cancer Inst. 89:718-23). In addition, I3C's use is associated with a number of safety concerns due to its enzyme-inducing and reproductive-toxic actions making it unacceptable for use in women of reproductive age (Dashwood, 1998, Chem Biol Interact. 110:1-5; and Gao et al., 2002, Toxicol Appl Pharmacol. 183:179-88).

One prominent product derived from I3C, and also present in cruciferous plants is 3,3'-diindolylmethane (DIM), the linear dimer molecule formed from the condensation of two molecules of I3C. Once formed, DIM is stable in acid and less enzyme inducing than other I3C products (Bradfield et al., 1987, J Toxicol Environ Health. 21:311-23). In cell culture, DIM has been shown to have apoptosis promoting effects in both estrogen-dependent and independent breast cancer cells (Hong et al., 2002, Biochem Pharmacol 63:1085-97). DIM has also been shown to specifically induce apoptosis in papillomavirus altered cervical cancer cell lines (Chen et al., 2001, J Nutr. 131:3294-302). In animals, orally administered DIM inhibits the growth of certain chemically induced forms of breast cancer (Chen et al., 1998, Carcinogenesis, 19:1631-9).

Investigations of DIM have resulted in U.S. Pat. No. 5,948,808, "Indole-3-carbinol, diindolylmethane and substituted analogs as antiestrogens", which provides for a method of treating estrogen-dependent cancer. U.S. Pat. No. 6,656,963, "Indole-3-carbinol (I3C) derivatives and methods", discloses additional derivatives of I3C for use in methods to inhibit cancerous cell growth, but specifically excludes DIM.

Previous experimental work by the present inventor has described the use of DIM and the related trimeric derivative of I3C, 2-(Indol-3-ylmethyl)-3,3'-diindolylmethane (LTR), in specialized formulations (U.S. Pat. No. 6,086,915) and in treatments for breast pain (mastalgia) and endometriosis (U.S. Pat. No. 6,689,387). Endometriosis is a disorder of uterine epithelial tissue (endometrium) which migrates outside the endometrial cavity of the uterus and resumes growth, typically in the abdomen. Pending applications of the present inventor also include uses of DIM and LTR for cervical dysplasia (U.S. patent application Ser. No. 10/616,477), and for Human Papilloma Virus (HPV) infections (U.S. patent application Ser. No. 10/616,477). Like endometriosis, cervical dysplasia and HPV infections are disorders of epithelial tissue and not smooth muscle. Leiomyomas are a distinct pathobiologic entity, arising only in uterine or extra-uterine smooth muscle which is a distinct tissue with different appearance, structure, function and embryologic origin than endometrium and other epithelial tissue.

A more recent patent application (U.S. Patent Application Publication No. 2003/0220377, filed May 7, 2003) describes synthetic indole anti-estrogenic compounds, structurally unrelated to DIM, which are proposed to treat both cancerous and benign conditions involving the uterus. In distinction to these synthetic, indole anti-estrogens, DIM has been shown to have estrogenic, growth promoting activity in breast cancer cells (Riby et al., 2000, Biochem Pharmacol. 60:167-77) and estrogen-receptor activating activity in endometrial cancer cells (Leong et al., 2004, Mol. Endocrinol. 18:291-302. Epub 2003 Nov. 26). Finally, U.S. Patent Application Publication No. 2001/0002393 (filed Dec. 20, 2000), describes methods and kits for treating and diagnosing leiomyomas using inhibitors of metalloproteinase enzymes.

It would be beneficial to have new therapeutic options for leiomyoma treatment that are non-invasive, that avoid or minimize surgery, and that avoid the side effects of systemically administered hormonal therapies. New medical therapies for the treatment leiomyoma-related conditions are needed.

3. SUMMARY OF THE INVENTION

The present invention provides compositions and methods of using diindolylmethane and diindolylmethane-related indoles to treat intra- and extra-uterine leiomyomas. The methods typically involve oral use of 3,3'-diindolylmethane (DIM) in an effective amount to reverse or retard the growth of leiomyomas. The methods, using pharmaceutically acceptable formulations, result in a reduction of the size of the myomas and a resolution of myoma-related symptoms. In certain embodiments, these methods employ structurally-related, synthetically-derived, substituted diindolylmethane compounds. Preferred DIM-related compounds for use in the methods and compositions of the invention include, but are not limited to, hydroxylated DIMs, methoxylated DIMs, 2-(Indol-3-ylmethyl)-3,3'-diindolylmethane (LTR), hydroxylated LTRs, methoxylated LTRs, 5,5'-dimethylDIM (5-Me-DIM), 2,2'-dimethylDIM (2-Me-DIM), 5,5'-dichloroDIM (5-Cl-DIM), imidazolelyl-3,3'-diindolylmethane, nitro-substituted imidazolelyl-3,3'-diindolylmethanes, 2,10-dicarbethoxy-6-methoxy-5,7-dihydro-indolo-[2,3-b]carbazole, 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole, and 2,6-dicarbethoxy-3,3'-dimethyl-13,14-diindolylmethane.

In preferred embodiments, DIM or the DIM-related indole is suspended as microparticles in a starch carrier matrix.

In certain embodiments, the methods and compositions of the invention involve the oral use of DIM and DIM-related compounds. In certain embodiments, DIM or the DIM-related indole is administered intra-arterially, vaginally, or is injected directly into myoma tissue.

In other embodiments, the compositions of the present invention useful in treating leiomyoma-related disease also include suspensions of DIM and related synthetic diindolylmethanes suitable for direct injection into leiomyoma tissue at the time of pelvic abdominal surgery or during trans-vaginal intra-uterine surgery (hysteroscopy). DIM releasing microspheres are also described for use during Uterine Artery Embolization (UAE) procedures.

In further embodiments, topical preparations of DIM and related diindolylmethanes are described for use in vaginal suppositories to treat leiomyomas. Vaginal suppository applications of DIM and related synthetic diindolylmethanes can be used alone or in conjunction with oral dosage forms for leiomyoma treatment.

In certain embodiments of the invention, the subject is a human. Human leiomyomas can be uterine leiomyomas or extra-uterine leiomyomas. In other embodiments, the subject is an avian. Suitable avians include, but are not limited to, chickens and quails. Avian leiomyomas are generally oviduct leiomyomas.

In another embodiment, the present invention describes oral use of DIM and related synthetic diindolylmethanes in conjunction with orally active antagonists of cellular growth factor receptors. This includes combined use of DIM with epidermal growth factor receptor (EGFR) antagonists. EGFR antagonists appropriate for combined use with DIM and/or synthetic derivatives of DIM, includes tyrosine-kinase EGFR inhibitors, such as ZD1839 (Gefitinib, Iressa®, [AstraZeneca, UK]), OSI-774 (Erlotinib, Tarceva®, [OSI Pharmaceuticals, Boulder, Colo.]), CI 1033 [Parke-Davis Pharmaceutical Research, Ann Arbor, Mich.], PKI 166 [Novartis Pharma, AG (Basel, Switzerland)] and others (e.g., GW2016; N-{3-Chloro-4-[(3-fluorobenzyl)oxy]phenyl}-6-[5-({[2-(methylsulfonyl)ethyl]amino}methyl)-2-furyl]-4-quinazolinamine). Other suitable EGFR receptor antagonists include those of natural origin with EGFR inhibiting activity such as silibinin, (−)-epigallocatechin-3-gallate (EGCG), resveratrol, and their cell growth inhibiting metabolites or derivatives.

In yet another embodiment, combination therapy for leiomyomas, included within the scope of this invention, includes the use of DIM and DIM-related compounds used with and without EGFR antagonists in conjunction with Uterine Artery Embolization (UAE), surgical myomectomy, and/or low-dose external beam radiation therapy. The object of combined use of DIM and DIM-related compounds with other treatment modalities for leiomyomas is to increase the efficacy over a single modality therapy alone.

4. BRIEF DESCRIPTION OF THE DRAWINGS

Figure 1B:
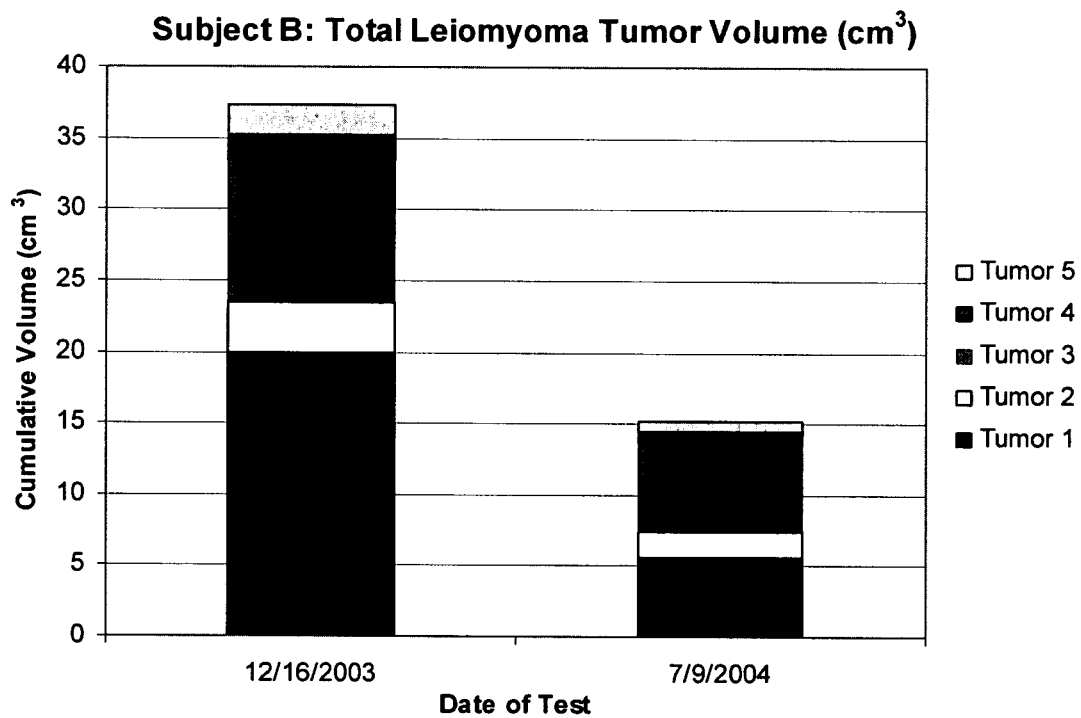

FIGS. 1A-B Reduction of leiomyoma tumor volume in patients treated with oral DIM. A. Subject A. B. Subject B.

5. DETAILED DESCRIPTION OF THE INVENTION

The present inventor has discovered that administration of DIM to a female or male having leiomyoma tissue results in retarding the growth and reducing the size of myoma tissue. In humans, myoma-associated symptoms, including pain, painful or excessive menstrual bleeding, and myoma-related bowel and urinary dysfunction improve following DIM-based treatment. Although rare, leiomyomas also develop outside the uterus in both women and men. Extra-uterine sites of leiomyoma occurrence include the nipple, esophagus, scrotum, and seminal vesicles which all possess smooth muscle (Farman, 1975, S Afr Med J. 49:1333-40). In avian species, DIM, or a DIM-related indole, is used to prevent or delay the development of leiomyomas of the oviduct and magnum, lengthening the period of breeding and egg production in economically important poultry.

5.1. Diindolylmethane and Diindolylmethane Related Indoles

In certain embodiments, the DIM compounds useful in the methods of the invention include DIM (3,3'-diindolylmethane) and the related linear DIM trimer (2-(indol-3-ylmethyl)-3,3'-diindolylmethane [also written: 2 (Indol-3-ylmethyl)-indol-3-yl]indol-3-ylmethane] (LTR). As used herein, "DIM-related compound", "DIM-related indole", and "DIM derivative" are used interchangeably, and refer to both natural metabolites and analogs of DIM, and also to "structurally-related, synthetically-derived, substituted diindolylmethane compounds" and "synthetic derivatives of DIM", such as those disclosed herein and known in the art. One of ordinary skill in the art will recognize that in any of the pharmaceutical compositions or methods of the invention where DIM is used, a DIM-related compound, including a structurally-related, synthetically-derived, substituted diindolylmethane compound or synthetic derivative of DIM, can be used.

The chemical structure of a DIM is as follows (where each of the R groups is H):

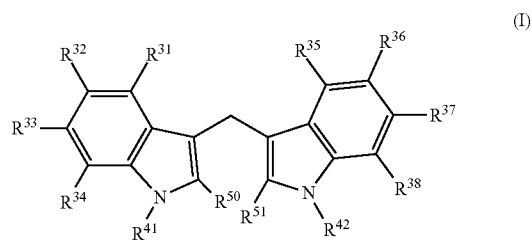

The chemical structure of LTR is as follows (where each of the R groups is H):

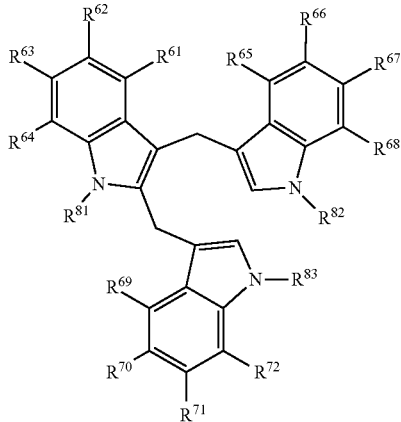

(II)

In certain embodiments, an active hydroxylated or methyoxylated metabolite of DIM, i.e., a compound of formula I, wherein $R_{32}$, $R_{33}$, $R_{36}$, and $R_{37}$ are substituents independently selected from the group consisting of hydrogen, hydroxyl, and methoxy, and $R_{31}$, $R_{34}$, $R_{35}$, $R_{38}$, $R_{41}$, $R_{42}$, $R_{50}$, and $R_{51}$ are hydrogen, is utilized.

In certain embodiments, an active hydroxylated or methyoxylated metabolite of LTR, i.e., a compound of formula II, wherein $R_{62}$, $R_{63}$, $R_{66}$, $R_{67}$, $R_{70}$, and $R_{71}$ are substituents independently selected from the group consisting of hydrogen, hydroxyl, and methoxy, and $R_{61}$, $R_{64}$, $R_{65}$, $R_{68}$, $R_{69}$, $R_{72}$, $R_{81}$, $R_{82}$, and $R_{83}$ are hydrogen, is utilized.

In an alternative embodiment, active DIM derivatives with $R_{32}$ and $R_{36}$ substituents made up of ethoxycarbonyl groups, and $R_{50}$, $R_{51}$ are either hydrogen or methyl, are utilized. In another embodiment, active substituted DIM derivatives including methylated and chlorinated compounds, exemplified by those that include 5,5'-dimethylDIM (5-Me-DIM), 2,2'-dimethylDIM (2-Me-DIM), and 5,5'-dichloroDIM (5-Cl-DIM) are described in U.S. Patent Application Publication No. 2002/0115708 by Safe, published Aug. 22, 2002, incorporated herein by reference in its entirety, are utilized in the present invention. In another embodiment, active DIM derivatives include imidazolelyl-3,3'-diindolylmethane, including nitro substituted imidazolelyl-3,3'-diindolylmethanes, and additional DIM-related compounds described in U.S. Patent Application Publication No. 2004/0043965 by Jong, Ling, published Mar. 4, 2004, incorporated herein by reference in its entirety, are utilized.

In certain embodiments, a DIM related compounds has formula (III):

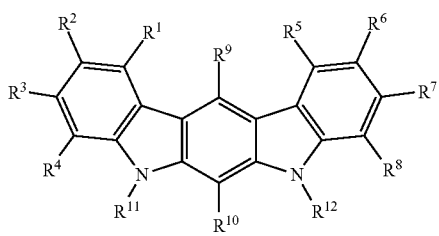

(III)

wherein:
$R^1$, $R^2$, $R^3$, $R^4$, $R^5$, $R^6$, $R^7$, $R^8$, $R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, with the provisos that: at least one of $R^1$, $R^2$, $R^3$, $R^4$, $R^5$, $R^6$, $R^7$, $R^8$, $R^9$, $R^{10}$, $R^{11}$ and $R^{12}$ is other than hydrogen; and when $R^1$, $R^2$, $R^3$, $R^4$, $R^5$, $R^6$, $R^7$, and $R^8$ are selected from hydrogen, halo, alkyl and alkoxy, then $R^{11}$ and $R^{12}$ are other than hydrogen and alkyl.

A preferred embodiment includes the use of 2,10-dicarbethoxy-6-methoxy-5,7-dihydro-indolo-[2,3-b]carbazole (SRI13668 (SRI Inc., Menlo Park, Calif.)). Additional preferred embodiments include the use of 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole (SRI Inc., Menlo Park, Calif.).

In another embodiment, a DIM related compounds has formula (IV):

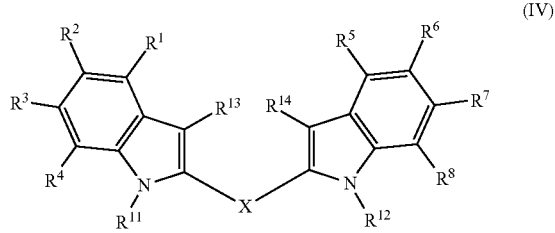

(IV)

wherein:
$R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl;

$R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen; and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$.

A preferred embodiment includes the use of 2,6-dicarbethoxy-3,3'-dimethyl-13,14-diindolylmethane (SRI Inc., Menlo Park, Calif.).

In another embodiment, a DIM related compounds has formula (V):

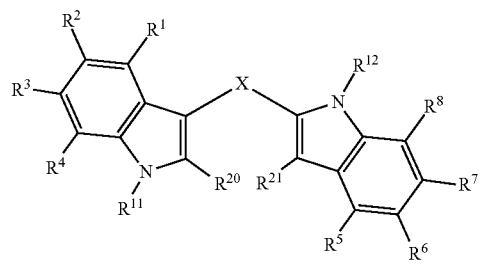

(V)

wherein:
$R^1$, $R^2$, $R^3$, $R^4$, $R^5$, $R^6$, $R^7$, $R^8$, $R^{11}$, $R^{12}$, and X are defined as for compounds of formula (III); and $R^{20}$ and $R^{21}$ are defined as for $R^1$, $R^2$, $R^3$, $R^4$, $R^5$, $R^6$, $R^7$, and $R^8$.

In yet another embodiment, the DIM-related indole is an indole-3-carbinol tetrameric derivative (Brandi et al., 2003, Cancer Res. 63:4028-4036).

5.2. Dosage and Administration

DIM or a DIM-related compound may be administered by any means and at any dosage, as described below. The actual administered amount of DIM or a DIM-related compound may be decided by a supervising physician or veterinarian and may depend on multiple factors, such as, the age, condition, file history, etc., of the subject, or patient, in question.

The subject, or patient, to be treated using the methods of the invention is an animal, e.g., avian (such as a chicken or quail) or a mammal, and is preferably human, and can be a fetus, child, or adult. In a preferred embodiment, the subject is a human female.

A preferred embodiment is the oral administration of DIM or synthetic derivatives in an acceptable formulation for oral administration. Preferably, the diindolylmethane used in the invention has been processed to enhance bioavailability, as is described in U.S. Pat. No. 6,086,915; however any suitable preparation of diidolylmethane or of a structurally-related, synthetically-derived, substituted diindolylmethane, can be used in the methods and compositions of the invention.

DIM is administered in a dose from 25-600 mg/day or 25-500 mg/day orally. DIM may be administered once per day, or two or more times per day. Preferably the dose is administered 2-3 times per day. Most preferably, the DIM is administered in a formulation designed for enhance oral absorption, e.g., microencapsulated with TPGS (as described in U.S. Pat. No. 6,086,915). This formulation (25-30% DIM by weight) is administered in a dose of 100-2000 mg/day, or more preferably at a dose of 300-600 mg, providing 75-150 mgs of actual DIM, given orally twice per day. As an alternative to DIM, the closely related linear trimer (LTR) may be employed in methods and doses described for DIM as a single agent for leiomyoma treatment. As a further alternative, the orally active DIM derivatives described in U.S. Patent Application Publication No. 2004/0043965 may be employed in the present invention as single agents. Structurally-related, synthetically-derived, substituted diindolylmethane's, as described by Jong (U.S. Pat. No. 6,800,655 and Patent Application Publication No. 2004/0043965) are administered according to the present invention in an acceptable formulation for oral administration in a dose of 10-400 mg/day. Preferably, these substituted diindolylmethanes are administered in an absorption-enhanced formulation at a dose of 50 to 250 mg/day.

In an alternative embodiment, DIM or a structurally-related, synthetically-derived, substituted diindolylmethane can be administered in the form of a sterile, injectable suspension. The suspension is injected directly into the leiomyoma tissue at the time of exploratory pelvic abdominal surgery, pelvic laparoscopy or hysteroscopy. Injection of the leiomyoma tissue is followed post operatively by oral use of DIM in an acceptable formulation and at an effective dose. Such a suspension consists of, for example, microcrystalline DIM or structurally-related, synthetically-derived, substituted diindolylmethanes (0.2-2% wt/volume) in a suspension of physiologic salts, and pH adjusters. Particle sizes of DIM or structurally-related, substituted diindolylmethane crystals in suspensions are from 50 to 500 microns in average diameter. pH adjusters such as NaOH are added to bring the pH to 7.5-8. Preferably, 1-2 cc of suspension containing 10-20 mg of DIM or a substituted diindolylmethane, depending on the size of the myoma, is injected directly into each leiomyoma.

In alternative embodiments for direct injection into fibroid tissue, DIM analogues, including imidazolelyl-3,3'-diindolylmethane, nitro substituted imidazolelyl-3,3'-diindolylmethanes and DIM-related compounds described in U.S. Patent Application Publication No. 2004/0043965 by Jong, Ling, published Mar. 4, 2004, can be used in manufacture of the sterile suspension. Preferably, 1-2 cc of suspension containing 0.001 mg/kg to 100 mg per kg of structurally-related, synthetically-derived, substituted diindolylmethane as described by Jong can be administered by direct injection into individual fibroid tissue masses.

In another alternative embodiment, injectable emulsions of DIM or a structurally-related, synthetically-derived, substituted diindolylmethane can be formulated to overcome the low solubility of DIM in both water and lipid. A specialized micro-emulsion utilizes phospholipids to optimize the solubility of DIM and related compounds and improve the stability of the emulsion. Preferably, 1-3 cc of a sterile, injectable emulsion containing 7-20 mg of DIM or substituted diindolylmethane is injected into each leiomyoma under direct vision, depending on the size of the myoma.

In another alternative embodiment, DIM or a structurally-related, synthetically-derived, substituted diindolylmethane can be incorporated within bio-compatible, stable microspheres for use during Uterine Artery Embolization (UAE). In one preferred use, DIM and/or EGFR-antagonists are included in the production of hydrophilic, non-resorbable, microspheres produced from an acrylic polymer and impregnated with porcine gelatin. Examples of production techniques for DIM-impregnated microspheres for controlled, targeted embolization of myomas are described in U.S. Pat. No. 5,635,215 and U.S. Patent Application Publication No. 2003/0211165 by Vogel et al., published Nov. 13, 2003, both of which are herein expressly incorporated by reference in their entireties. Dose ranges for administration of DIM and structurally-related, synthetically-derived, substituted diindolylmethanes, when used in microspheres as extended-release drug delivery devices, are from 25-2000 mgs per embolization treatment. When used in conjunction with EGF-antagonist impregnated microspheres, the dose range for administration of DIM or a DIM-related compound is 25-1000 mgs and the EGFR-antagonist dose is from 250-1000 mgs per embolization treatment. DIM and/or an EGFR inhibitor containing microspheres are ideally used in smaller size (50-500 micron diameters) and dose (less than 500-1000 mg total microsphere weight) than current inert microspheres which are recommended to be greater than 500 micron in diameter and to be used in doses greater than 1000 mg microsphere weight. Smaller active microspheres containing DIM and/or an EGFR inhibitor result in sub-total arterial blockage and reduce post-treatment side effects associated with ischemic tissue necrosis.

Following myomectomy, UAE, or low-dose radiation therapy, typical doses of oral DIM or a structurally related, synthetically-derived, substituted diindolylmethane are from 25-100 mg twice a day for 2-4 months. In an alternative embodiment, oral DIM and a structurally related, synthetically-derived, substituted diindolylmethane can be administered with orally active EGFR-antagonists. In one embodiment, DIM or a DIM-related compound is used with IRESSA® (Gefitinib [ZD1839]) for 1-4 months using an IRESSA dose of 50-100 mg/day.

In an alternative embodiment, DIM or a DIM-related compound can be suspended in a vaginal formulation such as a suppository for use, e.g., in myoma patients. Typically the suppository is placed high in the vagina once daily providing a dose from 250-1000 mg of DIM. In a preferred embodiment, once daily use of a 500 mg DIM vaginal suppository is continued for 2-6 months and accompanied by oral use of an absorption enhanced formulation of DIM in a dose of 300 mg twice daily providing 75 mg of DIM orally, twice daily.

5.3. Combination Therapy

As indicated, the methods and compositions of the present invention are also useful in combination with other therapeutic agents and therapeutic modalities which may be used for the treatment of leiomyomas. A combination of agents is expected to result in more effective therapy to be used for a shorter duration of treatment. Cell culture study of myoma cells using a polymerase chain reaction (PCR) demonstrated an excess in levels of epidermal growth factor (EGF) messenger RNA which was seen in proliferative phase tissue samples, compared to proliferative phase samples from normal uteri (Harrison-Woolrych et al., 1994, J Clin Endocrinol Metab. 78:1179-84). These results establish the dominant contribution of progesterone and elevations of EGF in the abnormal growth of myoma tissue.

5.3.1. EGFR Inhibitors

The EGFR inhibitors for use in the methods and compositions of the present invention include, but are not limited to, small molecule drugs which inhibit one or more EGFRs, monoclonal antibodies inactivating EGFRs, and antisense DNA or RNA inactivating EGFR DNA or RNA delivered to a cell using gene therapy. EGFRs which may be inhibited include any EGFR known in the art. See, e.g., Rajkumar, 2001, Current Science 81:535-541. Due to expected synergistic interaction of DIM, or a structurally-related DIM, with an EGFR inhibitor, reduced doses of an EGFR inhibitor can be used when used in combination with DIM.

In one embodiment, absorption-enhanced DIM or a structurally-related, synthetically-derived, substituted diindolylmethane is administered in conjunction with an orally active antagonist of the EGF receptor (EGFR). In a preferred embodiment, effective doses of DIM would be the same as used when DIM is administered alone. A representative dose is 15 mg DIM (60 mg of a typical formulated DIM) or 25 mg DIM (100 mg of a typical formulated DIM).

Small molecular EGFR inhibitors suitable for use in the invention include the EGFR inhibitors, Gefitinib (N-(3-chloro-4-fluorophenyl)-7-methoxy-6-(3-morpholinopropoxy)quinazolin-4-amine, Iressa, AstraZeneca, UK) and related compounds (see European Patent Application No. 0566226; International Patent Applications WO 96/33980 and WO 97/30034; Woodburn et al., 1997, Proc. Amer. Assoc. Cancer Research 38:633; and Woodburn et al., 1999, Pharmacol. Ther. 82, 241-250), Erlotinib (N-(3-ethynylphenyl)-6,7-bis(2-methoxyethoxy)quinazolin-4-yl]-(3-ethynylphenyl)amine, Tarceva®, OSI Pharmaceuticals [Boulder, Colo.]) and related compounds (see International Patent Applications WO 96/30347 and WO 99/55683), CI 1033 (6-acrylamido-N-(3-chloro-4-fluorophenyl)-7-(3-morpholinopropoxy) quinazolin-4-amine, Pfizer [New York, N.Y.]) and related compounds (see International Patent Applications WO 97/38983 and WO 00/31048, and Smaill et al., 1999, J. Med. Chem. 42:1803-1815), PKI 166 (4-[(1R)-1-phenylethylamino]-6-(4-hydroxyphenyl)-7H-pyrrolo[2,3-d-]pyrimidine, Novartis Pharma, AG [Basel]) and related compounds (see International Patent Application WO 97/02266) and GW2016 (N-{3-Chloro-4-[(3-fluorobenzyl)oxy]phenyl}-6-[5-({[2-(methylsulfonyl)ethyl]amino}methyl)-2-furyl]-4-quinazolinamine).

The specific EGFR's to be inhibited include the HER family of EGFR's, PDGFR (Platelet Derived Growth Factor Receptor), and VEGFR (Vascular Endothelial-derived Growth Factor Receptor). Representative specific small molecule drugs useful in the present invention, presented in relation to the EGFR inhibited are summarized in Table 1.

TABLE 1

Orally active, GRF Inhibitor Drugs for Use with DIM-Related Indoles:

| Drug | Manufacturer | Drug Class | HER EGFR I | II | IV | IV | VEGFR | PDGF |
|---|---|---|---|---|---|---|---|---|
| ZD1839 Gefitinib (Iressa) | AstraZeneca | Small Head Group Quinazoline (reversible) | X | | | | | |
| ZD6474 | AstraZeneca | | X | X | | | | |
| OSI-774 Erlotinib (Tarceva) | OSI/Roche/ Genentech | Small Head Group Quinazoline (reversible) | X | | | | | |
| Lapatinib GW-572016 | GlaxoSmithKline | Large Head Group Quinazoline | X | X | | | | |
| GW-2016 | GlaxoSmithKline | | X | X | | | | |
| STI-571 Imatinib Myesylate (Gleevec) | Novartis | | X | | | | | X |
| EKB-569 | Wyeth | (irreversible) | X | X | | | | |
| CI-1033 (PD183805) Cancertinib | Pfizer | 4-anilinoquinazoline (irreversible) | X | X | X | X | | |
| SU5416 Semaxanib | Sugen Pharma/Pfizer | indolin-2-ketone | | | | | X | |
| SU11248 | Sugen Pharma/Pfizer | indolin-2-one | | | | | X | X |
| SU6669 | Sugen Pharma | | X | | | | | |
| Vatalanib PTK787 (ZK222584) | Novartis/Schering | anilino-phthalazines | X | X | X | X | X | X |
| PKI-166 | Novartis | Pyrrolopyrimidines (reversible) | X | X | | | X | |
| CEP-7055 | Sanofi-Synthelab | Dimethylglycene | | | X | X | | |

Representative specific EGFR inhibiting monoclonal antibodies useful in the present invention presented in relation to the EGFR inhibited, include those that appear in Table 2.

TABLE 2

Representative EGFR-specific antibodies

| Drug | Manufacturer | Class | HER | VEGFR | PDGF |
|---|---|---|---|---|---|
| Cetuximab (Erbitux) | ImClone/B-MS | Mouse/human mAb | X | | |
| Trastuzumab (Herceptin) | Genentech/DNA | mAb | X | | |
| MDX-210 | Medarex | mAb | X | | |
| ABX-EGF | Abgenix/Immunex | mAb | X | | |
| TheraCIM | YM | mAb | EGFR | | |
| Panitumumab | AbBenix | mAb | EGFR | | |
| EMD-72000 | Merck | mAb | EGFR | | |
| bevacizumab (Avastin) | DNA/Hoffman | mAb | | X | |
| Ranibizumab (Lucentis) | DNA/Novartis | mAb | | X | |

Doses of an EGFR inhibitor on the order of ⅕ the dose when administered alone can be employed. Typically, Iressa® (Gefitinib) would be employed in a dose of 50-500 mg/day, more preferably, 50-250 mg/day, or 50-100 mg/day, as the EGF receptor antagonist. Alternatively, a low, effective dose of another growth factor antagonist such as OSI-774 (Erlotinib, Tarceva®), CI 1033 [Parke-Davis Pharmaceutical Research (Ann Arbor, Mich.), PKI 166 [Novartis Pharma, AG (Basel, Switzerland)] or GW2016 would be employed at doses of 25-500 mg/day. Using combined DIM/EGFR antagonist treatment permits a shortened treatment interval of 1-3 months. As an example of such combined therapy, an absorption-enhanced formulation of DIM in a dose of 300 mg [75 mg actual DIM] is taken orally twice daily along with a dose of 100 mg of Iressa (ZD1839, Gefitinib) taken once daily. Alternatively, oral absorption-enhanced DIM formulations or DIM-related derivatives can be used with a member of the tyrosine-kinase inhibitor class of EGF inhibitors, such as ZD1839 (Gefitinib, Iressa), OSI-774 (Erlotinib, Tarceva), CI-1033, and GW2016, using effective oral doses of the DIM-related compound and the EGF-antagonist.

Further details of the clinical use of EGF antagonists for combined use with DIM and/or DIM-related compounds are described in the following publications, incorporated herein by reference in its entirety (Janmaat et al., 2003, Oncologist 8:576-86; and Janmaat et al., 2003, Drugs Today (Barc) 39 Suppl C:61-80).

TABLE 3

Dose Ranges for Combined uses of DIM-Related Indoles and EGFR Inhibitors

| Drug | Manufacturer | Minimal Effective Dose Range (MED) mg/day | Average Tolerated Dose Range (ATD) mg/day | Maximal Tolerated Dose Range (MTD) mg/day |
|---|---|---|---|---|
| Formulated DIM (BR-DIM) | BioResponse | 25-150 | 150-500 | 500-1000 |
| ZD1839 Gefitinib (Iressa) | AstraZeneca | 25-150 | 150-350 | 350-750 |

TABLE 3-continued

Dose Ranges for Combined uses of DIM-Related Indoles and EGFR Inhibitors

| Drug | Manufacturer | Minimal Effective Dose Range (MED) mg/day | Average Tolerated Dose Range (ATD) mg/day | Maximal Tolerated Dose Range (MTD) mg/day |
|---|---|---|---|---|
| Lapatinib GW-572016 | GlaxoSmithKline | 175-500 | 500-900 | 900-1,800 |
| OSI-774 Erlotinib (Tarceva) | OSI/DNA/ Roche | 50-150 | 150-200 | 200-400 |
| Imatinib Myesylate (Gleevec) STI-571 | Novartis | 100-300 | 300-400 | 400-800 |
| CI-1033 Efalizumab Xanelin EKB-569 | Pfizer | 10-100 5-25 | 100-500 25-75 | 500-700 75-200 |
| PKI-166 | Novartis | 10-50 | 50-100 | 100-900 |
| Semaxanib SU5416 | Sugen Pharma/ Pfizer | 10-50 mg/m$^2$ | 50-100 mg/m$^2$ | 100-200 mg/m$^2$ |
| CEP-7055 | Sanofi-Synthelab | 25-100 | 100-400 | 400-1000 |

Alternatively, the combinations of DIM (or a DIM-related compound) and an EGFR antagonist of natural origin allows use of EGFR antagonists at maximal oral dose, due to greater safety and tolerability of EGFR inhibitors of plant origin. Examples of natural polyphenolic compounds with demonstrated inhibition of EGFR inhibitory activity include Silibinin, a flavolignan isolated from the fruits of *Silibum marianum* (Milk Thistle) (Silybin[3,5,7,-trihydroxy-2-[3-(4-hydroxy-3-methoxyphenil)-2-hydroxymethyl-1,4-benxodioxan-6-il]-chronan-4-one]; Sharma et al., 2001, Mol. Carcinog. 30:224-36), (−)-epigallocatechin-3-gallate (EGCG), a polyphenolic catechin found in green tea (Sah et al., 2004, J Biol. Chem. 279:12755-62) and resveratrol, a stillbene derivative commonly isolated from grapevines (*Vitis vinifera* L) and from *Polygonium cuspidatum* Sieb. Et Zucc (Japanese knotweed). Also useful are compounds related to resveratrol such as viniferins, piceatannol (3,4,3',5'-tetrahydroxystilbene), oxyresveratrol (2,3',4,5'-tetrahydroxystilbene), 4,4'-dihydroxystilbene, and cis- and trans-piceids which are also preferred for use in the present invention (Stewart et al., 2004, Invest. New Drugs 22:107-117). Doses of compounds related to resveratrol to be used in the methods and compositions of the invention are similar to doses used for resveratrol. In certain embodiments, silibinin, EGCG, or resveratrol can be incorporated with DIM-related indoles in vaginal suppositories for topical application in proximity to uterine leiomyomas.

TABLE 4

Dose Ranges for Combined uses of DIM-Related Indoles and EGFR Inhibitors of Natural Origin

| Drug | Manufacturer | Effective Dose Range (mg/day) |
|---|---|---|
| Formulated DIM (BR-DIM) | BioResponse, LLC | 25-750 |
| Silibinin (SiliPhos) | Indena, Inc. | 100-2000 |
| Resveratrol (RegrapeX) | Interpharma Praha | 100-2000 |
| EGCG | Various | 500-2000 |

Also useful in combination with DIM, or DIM-related indole, in treating Leiomyomatous conditions are extracts of *Scutellaria barbata D*. Don (SB), an herbal component of the traditional Korean medicine known as 'Ban-Ji-Ryun,' which demonstrate growth inhibitory activity in leiomyoma cell culture (Lee et al., 2004, Int Immunopharmacol. 4:447-54) and Evodiamine, an indole alkaloid component extracted from the fruit of Evodiae Fuctus (*Evodia rutaecarpa Benth*). The *Scutellaria* extract is typically given at a dose of 200-800 mg/day, and the Evodia extract is typically given in a dose of 300-800 mg/day, providing Evodiamine (40-200 mg/day).

Since the 4-hydroxy estrogen metabolites characteristics of leiomyoma tissue are pro-oxidants, selected anti-oxidant compounds are of further benefit for use in combined therapy with DIM. These include Lycopene, the major carotenoid found in tomatoes. Lycopene has demonstrated inhibition of leiomyoma-related smooth muscle tumors in the oviducts of Japanese quail (Sahin et al., 2004, Nutr Cancer.50:181-9). In addition, lycopene, and related beta-carotene, protect cells from the pro-oxidant effects of 4-hydroxy estrogen metabolites, known to be produced in leiomyoma tissue (Muzandu et al., 2005, Jpn J Vet Res. 52:173-84). Typically, Lycopene is administered in association with a DIM related indole in a daily dose range from 4-30 mg/day. Lycopene or a related carotenoid can also be incorporated in vaginal suppositories for topical application to the uterus via the uterine cervix.

The combinations of DIM (or a DIM-related compound) and an EGFR antagonist, with or without a carotenoid or *Scutellaria* extract, can be in the same composition for administering in combination concurrently, or in different compositions for administering concurrently but separately, or sequentially. When the compounds are administered sequentially, the compounds can be administered within several minutes, several hours or several days of each other.

The combined use of DIM, or a structurally-related, synthetically-derived, substituted diindolylmethane, and an EGFR-antagonist can be further combined with other interventional modalities of leiomyoma treatment. Interventional modalities of treatment preferably include myomectomy, UAE, and low dose radiation therapy. Myomectomy is performed during pelvic laparotomy, pelvic laparoscopy, or uterine hysteroscopy. Myoma tissue not amenable to removal during these procedures and so is injected directly during the procedure with suspensions of DIM, or a DIM related compound, or with suspensions of microspheres impregnated with DIM or a DIM related compound, optionally with an EGFR-antagonist. Surgery is followed by oral administration of DIM, or a DIM-related compound, alone or in conjunction with EGFR-antagonist. UAE can be performed using the standard administration of non-resorbable acrylic microspheres (Embosphere Microspheres [Biosphere Medical, Inc., Rockland, Mass.]) followed by 1-4 months of oral administration of DIM or a DIM-related compound alone or in conjunction with EGFR-antagonist such as IRESSA. In an alternative embodiment, UAE is performed utilizing a microsphere as described in Example 5 manufactured to contain and slowly release DIM or a structurally-related, synthetically-derived, substituted diindolylmethane. To administer DIM containing microspheres, a sterile suspension of microspheres is first mixed with non-ionic contrast media. Typically, a total dose of 1-3 cc of a suspension of microspheres having a diameter of 300-500 microns which contains 250-750 mgs of DIM, or a structurally-related, synthetically-derived, substituted diindolylmethane, is mixed with contrast media and injected into one or both uterine arteries using fluoroscopic guidance. Preferably, DIM impregnated microsomes would be used in combination with EGFR-antagonist impregnated microsomes to take advantage of anticipated synergistic growth inhibitory activities of the two therapeutic agents. Finally, the availability of lesion directed radiation therapy permits combined use of DIM and a structurally-related, synthetically-derived, substituted diindolylmethane during low dose radiation therapy to take advantage of anticipated radiation sensitizing activity of the DIM or DIM-related compounds and EGFR antagonists. In this combined use, an oral DIM formulation with or without an EGFR-antagonist is administered before, during, and after a series of radiation therapy treatments. In a preferred embodiment, "Gammaknife" or "Cyberknife" (Accuray, Inc., Sunnyvale, Calif.) radiation therapy technology is used to concentrate and focus the radiation beam limiting the radiation exposure of adjacent, bladder, ovarian, and intestinal tissue. Non-invasive radiation therapy treatment, limited to the myoma, is followed by oral treatment with oral DIM, structurally-related, synthetically-derived, substituted diindolylmethane's, optionally with IRESSA or other orally active EGF antagonist. Preferably, the cGy dose is held below the threshold dose known to cause damage to adjacent structures. A computer program such as the one described in U.S. Pat. No. 6,477,229 can be used to choose a safe cumulative radiation dose. Following Cyberknife radiation treatment, an absorption-enhanced formulation of DIM in a dose of 300 mg [75 mg actual DIM] is taken orally twice daily alone or with a dose of 50-100 mg of Iressa (ZD1839, Gefitinib) taken once daily.

5.4. Pharmaceutical Compositions

The pharmaceutical compositions according to the present invention preferably comprise one or more pharmaceutically acceptable carriers and the active constituents. The carrier(s) must be "acceptable" in the sense of being compatible with the other ingredients of the composition and not deleterious to the recipient thereof.

It will be appreciated that the amounts of DIM or a DIM-related compound required for said treatment will vary according to the route of administration, the disorder to be treated, the condition, age, and file history of the subject, the galenic formulation of the pharmaceutical composition, etc.

Preferably, the DIM or a DIM-related compound used in the invention has been processed to enhance bioavailability, as is described in U.S. Pat. No. 6,086,915. DIM or LTR processed in this manner is referred to as "processed DIM" and "processed LTR", respectively. However, any suitable preparation of DIM or a DIM-related compound can be used in the methods and compositions of the invention.

The following is a list of ingredients useful for formulating processed DIM or a DIM-related compound:

1. About 10 to about 40 percent by weight of DIM or a DIM-related compound.

2. About 10 to about 40 percent by weight of the following, alone or in combination: vitamin E succinate polyethylene glycol 1000; vitamin E succinate Polyethylene glycols with polyethylene glycol (with a molecular weight range of 400-2000); other polyethylene glycol esters such as those formed by fatty acids such as oleic acid or stearic acid; polyvinylpyrrolidones; polyvinylpolypyrrolidones; Poloxamer 188, Tweens; or Spans.

3. About 5 to about 20 percent by weight of the following, alone or in combination: phosphatidyl choline (derived from soy lecithin and supplied as Phospholipon 50G from Rhone Poulenc Rorer); dioleoyl phosphatidylcholine; phoshatidylglycerol; dioleoylphosphatidylglycerol; dimyristoylphosphatidylcholine; dipalmitoylphosphatidylcholine; phosphatidylethalolamines; phosphatidylserines; or sphingomyelins; or other sources of phospholipids as those from purified Milk Fat Globule Membrane; glycerolesters; poly glycerol esters; or ethoxylated castor oil.

4. About 15 to about 30 percent by weight of the following, alone or in combination: hexanol; ethanol; butanol; heptanol; 2-methyl-1-pentanol; various ketone solvents that would be acceptable in foods such as methyl ethyl ketone, acetone and others; propylene glycol; and certain ester solvents such as ethyl acetate.

5. About 20 to about 40 percent by weight of the following, alone or in combination: modified starch such as Capsul™ Starch from National Starch, Inc.; methylcellulose; hydroxypropyl methylcellulose; hydroxyethylcellulose; hydroxypropylethylcellulose; pectin; gum arabic; gelatin; or other polymeric matrix-forming preparation known to those skilled in the art, soluble in water and, suitable for spray drying.

6. About 0.5 to about 35 percent by weight of the following, alone or in combination: aerosil 200; or any other flow enhancing excipient from silica, or related salt, known to those skilled in the art.

The following is a detailed method of formulating processed DIM:

1. 6.75 kg of TPGS is heated just beyond its melting point with constant stirring in a heated vessel ("First vessel").

2. 9.38 kg of hexanol and 9.83 kg of jet milled DIM is added to the first vessel and the mixture stirred to a uniform suspension at 70° C. 1.4 kg of phosphatidyl choline is then added.

3. In a second larger vessel, 185 L of water and 10.7 kg of starch are thoroughly mixed with a Cowles blade. This mixture is neutralized to pH 7 with a small amount of sodium carbonate and then heated to 75° C. and stirred for 1 hour.

4. The contents of the first vessel is added to the starch mixture in the second larger vessel and thoroughly mixed with a homogenizing rotor/stator type mixer at moderate speed for 15 minutes.

5. The mixture from step 4 is spray dried with a small amount (approximately 0.5%) of hydrophilic silica to provide a free flowing powder of finely dispersed microparticles containing the co-precipitated TPGS, phosphatidyl choline and DIM in an amorphous, non-crystalline structure.

6. The flowable powder product is collected and stored in evacuated foil sacks, after de-aerating and flushing with nitrogen.

7. Analysis of presence of unchanged dietary ingredient, reveals about 30 to about 33 percent by weight of DIM.

The procedure of making processed DIM may be summarized as follows:

(a) heating one or more solubilizing emulsifiers selected from the group consisting of vitamin E succinate polyethylene glycol 1000, polyvinylpyrrolidone, polyoxyethylene stearate, sodium cholate, deoxycholate and taurocholate;

(b) adding to the product of step (a) a solvent and a surfactant phospholipid selected from the group consisting of phosphatidyl choline, dioleoyl phosphatidyl choline, phosphatidylglycerol, dioleoylphosphatidylglycerol, dimyristoylphosphatidylcholine, dipalitoylphosphatidylcholine, phosphatidylethanolamine, phosphatidylserine and sphingomyelin to produce a solution;

(c) dissolving in the solution of step (b) LTR and/or DIM;

(d) adding to the solution of step (c) a solution containing an encapsulator;

(e) mixing the solution produced in step (d) to produce a microdispersion with a particle size of 5 microns or less; and (f) spray drying the resulting mixture to leave a solid hydrophobic phytochemical composition.

In general, a suitable (therapeutically effective) amount of DIM or LTR is 50-500 mg per day. DIM is preferably administered in an absorption enhancing formulation, as described in U.S. Pat. No. 6,086,915, at 50-200 mg per day, more preferably 400-800 mg per day, as a suspension of microparticles in a starch carrier matrix. The LTR is preferably administered in an absorption enhancing formulation at 50-200 mg per day, more preferably 200-800 mg per day, as a suspension of microparticles in a starch carrier matrix. The actually administered amounts of phytochemical may be decided by a supervising physician or veterinarian.

Therapeutic formulations include those suitable for parenteral (including intramuscular and intravenous), intra-arterial, oral, rectal, intra-vaginal, or intradermal administration, although oral administration is the preferred route. Thus, the pharmaceutical composition may be formulated as parenteral suspension, degradable and non-degradable microspheres for intra-arterial administration during UAE, tablets, pills, syrups, capsules, suppositories, formulations for transdermal application, formulations for intradermal uses, powders, especially lyophilized powders for reconstitution with a carrier for intravenous administration, feed pellets for veterinary use, etc.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Therapeutic formulations suitable for oral administration, e.g., tablets and pills, may be obtained by compression or molding, optionally with one or more accessory ingredients. Compressed tablets may be prepared by mixing DIM or a structurally-related, synthetically derived, substituted diindolylmethane, and compressing this mixture in a suitable apparatus into tablets having a suitable size. Prior to the mixing, the DIM or structurally-related DIM may be mixed with a binder, a lubricant, an inert diluent and/or a disintegrating agent.

In a preferred embodiment, DIM or a structurally-related, synthetically derived, substituted diindolylmethane is mixed with a binder, such as microcrystalline cellulose, and a surfactant, such as sodium lauryl sulphate until a homogeneous mixture is obtained. Subsequently, another binder, such as polyvidone, is transferred to the mixture under stirring with a small amount of added water. This mixture is passed through granulating sieves and dried by desiccation before compression into tablets in a standard tableting apparatus.

A tablet may be coated or uncoated. An uncoated tablet may be scored. A coated tablet may be coated with sugar, shellac, film or other enteric coating agents.

Therapeutic formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising phytochemical that is to be reconstituted by dissolving in a pharmaceutically acceptable carrier that dissolves said phytochemical.

When the pharmaceutical composition is a capsule, it may contain a liquid carrier, such as a fatty oil, e.g., cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides.

In yet another embodiment, the therapeutic compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321: 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105).

For use in UAE and myoma tissue injection, stable, biocompatible microspheres, easily injected through needles and angiography catheters, are preferred. Microspheres with diameters from 10 to about 300 micrometers in diameter are most preferred. Due to the poor water solubility of DIM and structurally-related, synthetically-derived, substituted diindolylmethanes, a method for preparation of biodegradable polymeric drug delivery devices using relatively low temperatures and non-aqueous solutions is useful. Techniques for manufacture of microspheres appropriate for the physicochemical characteristics of DIM, LTR, and synthetic DIM-related drugs are described in U.S. Pat. No. 5,718,921, which is incorporated by reference herein in its entirety. Manufacture of appropriate microspheres with desirable sustained release characteristics containing DIM or a structurally-related, synthetically-derived, substituted diindolylmethane, and/or EGFR-antagonist is further described in U.S. Patent Application Publication No. 2003/0211165 by Vogel et al., published Nov. 13, 2003, which is incorporated herein by reference in its entirety. Alternatively, embolic compositions comprising macromers having a backbone of a polymer having units with a 1,2-diol and/or 1,3-diol structure which incorporate DIM or a structurally-related, synthetically-derived, substituted diindolylmethane, and/or EGFR-antagonists can be made according to U.S. Patent Application Publication No. 2003/0223956 by Goupil et al., published Dec. 4, 2003, which is incorporated herein by reference in its entirety.

In other embodiments, a controlled release formulation comprising biodegradable polymer microspheres or microparticles wherein DIM or a structurally-related, synthetically-derived, substituted diindolylmethane is suspended in a polymer matrix, the polymer matrix being formed from at least two highly water soluble biodegradable polymers, and the microspheres being coated with a (d, 1 lactide-glycolide) copolymer is preferred. The selection of the particular (d, 1 lactide-glycolide) copolymer will depend in a large part on how long a period the microsphere is intended to release the active ingredient. For example, a (d, 1 lactide-glycolide) copolymer made from about 80% lactic acid and 20% glycolic acid is very stable and would provide a microsphere suitable for release of DIM, LTR, and synthetic DIM-related drugs over a period of weeks.

Other controlled release systems are discussed in the review by Langer (1990, Science 249:1527-1533).

In one embodiment of the pharmaceutical composition according to the invention, two or more active constituents are comprised as separate entities.

The invention also provides a pharmaceutical pack or kit comprising one or more containers filled with one or more of the ingredients for practicing the methods of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The invention is further explained by the following illustrative examples.

6. EXAMPLE 1

Manufacture of an Absorption-Enhanced Formulation of Dim for Treatment of Leiomyomas In general, a suitable (therapeutically effective) amount of diindolylmethane is preferably administered in an absorption enhancing formulation, as described in U.S. Pat. No. 6,086,915, at 100-2000 mg per day as a suspension of microparticles in a starch carrier matrix. The actually administered amounts of Diindolylmethane may be decided by a supervising physician.

Preparation of Processed Diindolylmethane was Accomplished According to the steps outlined in U.S. Pat. No. 6,086,915, herein incorporated by reference in its entirety. Briefly, this included mixture of about 10-40% by final weight of either diindolylmethane with about 10-40% by final weight of vitamin E polyethylene glycol 1000 succinate (Vitamin-E-TPGS, Eastman Chemical), 2-20% by final weight, phosphatidyl choline (Phospholipon 50G, Rhone Poulenc) and 15-30% by final weight hexanol. This mixture was made homogeneous by mixing. The homogeneous mixture of indoles and other oil soluble substituents listed above was added to a solution of modified starch in water (Capsul Starch from National Starch, Inc.). The starch component forms from 30-70% of the final dry weight of the product. The well dispersed final combined mixture was then subjected to spray drying. The resultant product was a fine powder containing either diindolylmethane contained within the starch particles.

Alternatively, the starch component described above as Capsul Starch from National Starch, Inc., can instead be made using Maltodextrin NF (Maltrin M100, GPC), 20-30% of the final dry weight, together with Gum Arabic USP/NF (TIC Pretested, TIC Gums), 20-30% of the final dry weight, together making 40-70% of the final dry weight. Additionally, fumed silica (Aerosil 200, Degussa), 1-2% of the final weight, can be added during the spray drying process as a flow aid.

7. EXAMPLE 2

Manufacture of Capsules Containing Diindolylmethane

Capsules containing 150-300 mg of processed diindolylmethane, as produced according to the steps described in Example 1, were made by mixing the processed diindolylmethane with microcrystalline cellulose and placing the mixed powder into opaque gelatin capsules.

Alternatively, capsules containing processed diindolylmethane (DIM), as produced according to the steps described in Example 1, were made by mixing the processed DIM with polyphenolic EGFR inhibitory compounds according to the following per capsule amounts. The ingredients are mixed according to these amounts and capsules are filled using standard machinery.

TABLE 5

| Component | Preferred Capsule Weight (mg) | Range of Capsule Weight (mg) |
| --- | --- | --- |
| Processed DIM | 75 | (50-100) |
| Silibinin (SiliPhos) | 100 | (100-200) |
| Green Tea Extract (EGCG) | 150 | (150-300) |
| Total Active Fill Weight (mg) | 325 | (300-625) |

Optionally, 6-25 mg of Lycopene is added to each capsule and/or 25-100 mg of *Scutellaria barbata* or *Evodia rutaecarpa* extract is additionally added as desired by the formulator. 1-6 capsules of the combined formulation are taken, preferably twice daily, with water as advised by a health care practitioner or label instructions.

8. EXAMPLE 3

Manufacture of a Vaginal Suppository Formulation of Dim for Treatment of Leiomyomas in Conjunction with Oral Therapy In a heated vessel, 90 grams cetostearyl alcohol (Alfol 16/18, Vista) was heated to 100° C. to which 5 gms of microcrystalline DIM (LKT Labs, St. Paul, Minn.) was added with constant mixing to form a hot slurry. Alternatively, 90 grams cetostearyl alcohol (Alfol 16/18, Vista) is heated to 100° C. to which 5 gms of microcrystalline DIM is mixed, alone or together with 10 grams of ceramide or synthetic cerimide derivatives, C2 ceramide. In a second vessel 400 gms of IV Novata (Semi-synthetic Glyceride Suppository Base, Ashland Chemicals) was warmed to 40° C. with constant mixing. The well mixed slurry from the first vessel was added with continued mixing to the second vessel. The homogenized molted suppository material was formed into suppositories of 2 gms each and cooled. Glyceryl monsterate 10-50 gms was added to the molten mixture as needed to increase the firmness of the final suppositories.

Alternatively, vaginal suppositories are produced using microcrystalline DIM as described above, combined with silibinin, resveratrol, or pharmaceutical EGFR antagonist (e.g., Gefitinib) to provide a minimally effective dose for the particular EGFR inhibitor (25-500 mg) per 2 gm suppository.

9. EXAMPLE 4

Manufacture of an Injectable Emulsion Formulation of Dim for Treatment of Leiomyomas To prepare a DIM emulsion for injection into leiomyomas, Ethyl oleate (EO), Phosphatidyl Choline (PC) (from egg yolk), and calcein, is purchased from Sigma-Aldrich, Inc (St. Louis, Mo.). Distearoyl-phosphatidylethanolamin-N-poly (ethyleneglycol) 2000 (DSPE-PEG) is purchased from Avanti Polar Lipids (Alabaster, Ala.).

Using a modification of the method of Yu et al. (Yu W et al., 1993, Int. J. Pharm. 89:139-146), the microemulsion is manufactured as follows: 160 grams of EO and 60 grams of PC are dissolved in 1 liter pure ethanol. 24 grams of microcrystalline DIM (mean particle size 0.25 micron) is added and is dissolved in this "oily phase". 20 grams of DSPEG-PEG is then dissolved in 500 cc of USP water (Aqueous phase). The oily ethanolic solution (oily phase) with the dissolved DIM is then slowly added into the DSPE-PEG solution (aqueous phase) under moderate magnetic stirring. The aqueous phase immediately turns milky with opalescence as the result of the microemulsion produced. The microemulsion is then subjected to low pressure at 360 mm Hg and maintained at 50° C. The low pressure is used to concentrate the emulsion through removal of the ethanol and a portion of the water. Using an infrared absorption assay to determine the DIM content of the microemulsion, a final concentration of DIM of 7.5 mg/ml is established. Sodium hydroxide is added to increase the pH to the 5.0-7.5 range.

Using this manufacturing technique emulsions of DIM are prepared and are subjected to stability testing to demonstrate that the particle size within the emulsion remains between 150 and 200 nm. The production technique results in a microemulsion with % weight ranges of the components in the following preferred ranges:

| Component | Approx % Weight |
| --- | --- |
| DIM | 0.05-0.1 |
| Lipids (EO:PC:DSPE-PEG; 8:3:1) | 45-28 |
| Water | 50-70 |
| Ethanol | 1-2 |

Alternatively, an ethanol-free production method can be utilized to produce a stable micro-emulsion of DIM or DIM derivatives and analogues, using Lipofundin MCT B. Braun Melsungen AG (Melsungen, Germany), a preformed basic emulsion, and high pressure homogenization of microcrystalline DIM. This method utilizes jet-milled DIM, with particle size reduced to 0.1 micron average diameter (performed by Micron Technologies, Inc., Exton, Pa.). Using this technique 700 mg of 0.1 micron diameter DIM crystals are homogenized in 100 cc Lipofundin using equipment and methods as described (Akkar et al., 2003, Eur J Pharm Biopharm. 55:305-12). This will result in a stable lipid-based micro-emulsion with particle size less than 200 nm and a DIM content of 7 mg/cc of the emulsion.

10. EXAMPLE 5

Manufacture of Stable Microspheres Containing Dim for Treatment of Leiomyomas During Selective Uterine Artery Embolisation (UAE)

Due to the poor water solubility of DIM, a production technique for stable, biocompatible microspheres containing DIM is developed based on production technology described in U.S. Pat. No. 5,718,921, herein expressly incorporated by reference in its entirety. This process uses a polyanhydride polymer which is dissolved in a volatile organic solvent, in which the DIM or structurally-related, synthetically-derived, substituted diindolylmethane is dispersed and co-dissolved in the polymer solution. The mixture is suspended in an organic oil, and the organic solvent is extracted into the oil, creating microspheres. The method enables the preparation of DIM containing microspheres from a variety of biodegradable polymers, including hydrophobic polyanhydrides such as (pCPP:SA, 50:50) and CPP copolymerized with dodecanedoic acid (DD), (pCPP:DD, 20:80) and (pCPP:DD, 50:50).

For the preparation of DIM microspheres, four grams of the polymer, pCPP:SA, 20:80, mw=16000, is dissolved in 20 ml methylene chloride, to which is added 1 gram of microcrystalline DIM and suspended in the polymer solution using a mechanical stirrer. The mixture is then dropped into silicon oil (Dow Chemical Company, Midland, Mich.) that contains between approximately 1.0 and 20% of Span™ or another surfactant or emulsifying agent. Span™ emulsifiers are preferred. This is then stirred at a set stirring rate. Stirring is done using an overhead stirrer type RZR50, ("CAFRAMA", Wiarton, Ont.) and a three-blade impeller. After 1 hour, petroleum ether is introduced and stirring is continued for another hour. The microspheres are isolated by filtration, washed with petroleum ether, dried overnight in a lyophilizer (Labconco, Freeze Dryer 8), are sieved (U.S. Standard Sieve Series, Newark, Wire Cloth Company, Newark, N.J.) and are stored at less than 0° C.

This process of manufacture will yield DIM impregnated microspheres with diameters of from 50 to 1000 microns. The recovery in this production process can be limited to 50% due to some polymer precipitating on the stirrer. The DIM microspheres are sieved to remove microspheres with diameters greater than 500 microns to result in microspheres with a final size distribution of 50-500 microns. The smaller microspheres are then sieved to remove those with diameters less than 50 microns, leaving microspheres with diameters between 500 and 500 microns. The resulting 2 grams of microspheres are again dried in a lyophilizer, autoclaved to sterilize, and resuspended at a concentration of 1.0 ml of microspheres in 5 ml of sterile physiological saline. The 5 ml suspension of microspheres will contain approximately 250 mgs of DIM, adequate for therapeutic use in a single UAE procedure.

11. EXAMPLE 6

Use of Oral, Absorption-Enhanced Dim for the Treatment of Leiomyomas in a Woman Application of orally active formulations of DIM or synthetic DIM derivatives is illustrated by the following clinical example of successful treatment of a myomatos condition.

A 44-year old female was symptomatic from uterine leiomyoma, experiencing painful menses with excessive bleeding, frequency of urination, and inability to exercise due to tiredness. Physical examination by her gynecologist revealed a right pelvic mass visible on inspection of the abdomen and palpable with gentle physical exam. Her pelvic exam revealed visible and palpable distortion of the uterine cervix due to protruding leiomyoma tissue. Bimanual palpation revealed a clearly enlarged uterus with an irregular contour consistent with multiple leiomyomas. A blood test indicated mild anemia. Hysterectomy was strongly suggested. The patient initiated therapy with capsules of DIM, formulated for enhanced absorption as described in Example 1. A dose of 120 mg of DIM formulation, given three times per day, delivering 30 mg of actual DIM per dose, was used. After two months of DIM use, the patient returned to her physician describing normal menstrual flow with normal levels of discomfort and improved energy. Her repeat physical exam included a normal abdominal exam with no visible or palpable pelvic masses. Her repeat pelvic exam showed a normal appearing uterine cervix and a palpable uterus of much reduced size.

12. EXAMPLE 7

Use of Oral, Absorption-Enhanced Dim to Reduce the Size of Uterine Leiomyomas Clinical treatment and laboratory study are being used to demonstrate the therapeutic benefits of oral DIM for leiomyoma patients associated with a reduced production of 4-hydroxy estrogen metabolites. Expected results are clinical improvement in symptoms and reduction of leiomyoma size documented in serial sonograms. Clinical treatment, using oral DIM formulated for enhanced absorption according to Example 1, has demonstrated meaningful reduction of leiomyoma size demonstrated by serial pelvic ultrasound evaluation.

Women with uterine leiomyomas have been selected based on the findings of abnormal uterine sonograms showing measurable leiomyoma documented on more than one occasion. Three subjects were proceeding to provide a baseline 12-hour urine collection and began to take absorbable DIM 150 to 450 mg [37.5-112 mg actual DIM] twice daily for 3-6 months. Two women have completed participation in a preliminary study, completing 2 and 6 month treatment periods. Subject A was a 46 yr old multiparous female with regular menstrual periods, taking thyroid hormone replacement to correct primary hypothyroidism and using no other medications. Subject B was a 50 year old female taking no medications with regular periods.

After informed consent, a pretreatment ultrasound was obtained for each subject. Each subject provided a 12 or 24 hour urine specimen which was frozen. Subject A began taking 2 capsules twice daily of absorption-enhanced DIM (BioResponse, LLC, Boulder Colo.) providing DIM at 100 mg/kg per dose. Subject B took 3 capsules twice daily of absorption-enhanced DIM (BioResponse, LLC, Boulder Colo.) providing DIM at 150 mg/kg per dose. After 2 months of treatment, Subject A was re-evaluated by the same ultrasound technician using the same equipment and at the same phase of her menstrual cycle. A post treatment urine was also obtained, collected at the same point in the menstrual cycle as the baseline urine sample. Similarly, Subject B was re-evaluated after 6 months of treatment using absorption-enhanced DIM (BioResponse-DIM). She took a higher twice daily dose providing 150 mg/kg/dose. Her re-evaluation included pelvic ultrasonography following a series of 3 pre-treatment pelvic ultrasound evaluations all performed with the same equipment. Like Subject A, Subject B provided a before and after DIM treatment urine sample.

The pelvic ultrasound data were analysed using a mathematical formula to calculate the pre-treatment and post-treatment volume of individual leiomyoma based on the widest diameter and the diameter perpendicular to this measured in centimeters (cm). A calculation of individual tumor volume was performed, treating each tumor as an ovoid mass, using the formula: $V=4/3\pi(H/2)^2(L/2)$, where V=volume in cubic centimeters ($cm^3$), H=tumor height in centimeters (cm), and L=tumor length in centimeters (cm). This method provided individual tumor volumes in cubic centimeters ($cm^3$). Results for the pre and post treatment tumor volumes with percent reduction following the 2 month treatment of Subject A and the 6 month treatment of Subject B are presented in Table 6 and 7 and FIGS. 1A-B. The average percent reduction in tumor volume was 33.5% for Subject A. The average reduction in tumor volume was 78.6% for Subject B.

TABLE 6

Leiomyoma Tumor Volumes in Subject "A" Before and After DIM Treatment

| Tumor Identification Number Subject "A" | Pre-DIM Treatment Tumor Volume ($cm^3$) | Post-DIM Treatment Tumor Volume ($cm^3$) | Percent Decrease in Tumor Volume |
| --- | --- | --- | --- |
| Tumor 1 | 22.39327 | 3.783001 | 83.10653 |
| Tumor 2 | 116.8987 | 114.4901 | 2.060378 |
| Tumor 3 | 62.83185 | 53.20497 | 15.32167 |

TABLE 7

Leiomyoma Tumor Volumes in Subject "B" Before and After DIM Treatment

| Tumor Identification Number Subject "B" | Pre-DIM Treatment Tumor Volume ($cm^3$) | Post-DIM Treatment Tumor Volume ($cm^3$) | Percent Decrease in Tumor Volume |
| --- | --- | --- | --- |
| Tumor 1 | 19.8836635 | 5.57528 | 71.9605 |
| Tumor 2 | 3.591364 | 1.876578 | 47.74749 |
| Tumor 3 | 9.91067762 | 6.093643 | 38.51437 |
| Tumor 4 | 1.88495559 | 0.884882 | 53.05556 |
| Tumor 5 | 2.11848065 | 0.796394 | 62.40732 |

The urine samples were tested at the Bradlow/Sepkovic Laboratory, Hackensack University Medical Center, Hackensack, N.J. The technique utilized was an established gas chromatography-mass spectrometry (GCMS) assay for estradiol (E2), estrone (E1), 2-hydroxy estrone (2OH-E1), 4-hydroxy estrone (4OH-E1), 16-hydroxy estrone (16OH-E1), and estriol (E3) in urine (Michnovicz et al., 1997, J Natl Cancer Inst. 89(10):718-23). The procedure involved overnight incubation with glucuronidase to glucouroides and subsequent analysis by derivitasation and GCMS determination of nanogram per milliliter of urine per 24 hours (ng/ml/24 hr). Laboratory analysis is expected to show an increase in 2-hydroxy estrone, and a decrease in 16-hydroxy estrone, as measured in pre-treatment as compared to post-treatment urine samples. A decrease in 4-hydroxy estrone would be consistent with inhibition of estrogen metabolism characteristic of leiomyomas (Liehr et al., 1995, Proc Natl Acad Sci USA. 92:9220-4). Results of before and after DIM treatment are presented in Table 8, showing the metabolites of interest as a percent of the total estrogen metabolites measured and as ratios of the amounts of 2OH-E1 to 16OH-E1 (2OH-E1/16OH-E1) determined for each sample. Comparison of results revealed large treatment related increases in 2OH-E1 and the 2OH-E1/16OH-E1 ratio in both Subjects. Subject A showed a treatment related reduction in 16OH-E1 and Subject B, treated at a higher dose, showed a treatment related reduction in 4OH-E1. 2OH-E1 estrogen metabolites are non-growth promoting, and weaker estrogens compared to 16OH-E1 and 4OH-E1.

TABLE 8

Percent or Ratio of Measured Estrogen Metabolites

| Subject (Dose and Duration) | Estrogen Metabolite or Metabolite Ratio | Before DIM | After DIM |
|---|---|---|---|
| "A" (200 mg/day DIM, Taken for 2 Months) | 2OH-Estrone (2OH-$E_1$) | 4% | 8.3% |
| | 4OH-Estrone (4OH-$E_1$) | 0.4% | 0.7% |
| | 16OH-Estrone (16OH-$E_1$) | 8.4% | 4.9% |
| | 2OH-$E_1$/16OH-$E_1$ | 0.5 | 1.7 |
| "B" (300 mg/day DIM, Taken for 6 Months) | 2OH-Estrone (2OH-$E_1$) | 2.5% | 35% |
| | 4OH-Estrone (4OH-$E_1$) | 2.5 | 1.7% |
| | 2OH-$E_1$/16OH-$E_1$ | 0.3 | 9.5 |

In conclusion, preliminary treatment of women with oral DIM resulted in a consistent reduction of intra-uterine leiomyoma size. Unlike the use of injected GnRN agonists (Flierman et al., 2005, BJOG. 112:638-42), or long acting progestins (Venkatachalam et al., 2004, J Obstet. Gynaecol. 24:798-800), the reduction in leiomyoma volume seen with DIM treatment was not associated with amenorrhea, hypoestrogenemia, hot flashes, or other reported side effects.

Further prospective, placebo-controlled clinical study of oral DIM in selected Leiomyoma patients will be used to further establish the utility of DIM-related methods of leiomyoma treatment.

13. EXAMPLE 8

Organ Culture of Uterine Leiomyoma Tissue Treated with Dim and/or Egf Antagonists An in vitro study of the effects of DIM and EGFR inhibitors will be undertaken. A protocol to establish the activity and synergism of DIM, and/or Gefitinib (Iressa®, ZD1839 [Astra Zeneca]) and other EGFR inhibitors, based on the exposure of primary cultures of leiomyoma tissue, is designed. These studies will utilize sex steroid supported growth of leiomyoma tissue in organ culture as a pre-clinical model. Iressa® is an orally active EGFR-TKI (epidermal growth factor receptor tyrosine kinase inhibitor) which blocks signal transduction pathways which may contribute to leiomyoma growth. Other inhibitors of the epidermal growth factor receptor (EGFR) to be tested include CI-1033 [Parke-Davis Pharmaceutical Research (Ann Arbor, Mich.)], a quinazoline tyrosine kinase inhibitor different from Iressa, and PKI 166 [Novartis Pharma, AG (Base1)], a non-quinazoline EGFR antagonist. The effects of DIM alone and in combination with an EGFR antagonist on leiomyoma cell growth are evaluated using the EVA/PCD (ex vivo apoptotic/programmed cell death) assay (Rational Therapeutics Cancer Evaluation Laboratories, Long Beach, Calif.) which has previously been shown to correlate with response, time and survival in patients with certain tumors.

Dose-response curves are interpolated to provide 50% lethal concentrations (LC(50)). The degree of synergy (by median effect) and normalised Z-scores (raw scores converted to relative activity distributed around the mean) is then computed.

Favorable interactions are anticipated for DIM combinations with EGF receptor antagonists. Leiomyoma cultures will be analyzed for synergistic increases in apoptosis-related cell killing with combinations of DIM and EGFR inhibitors. These primary leiomyoma culture studies may support synergistic and possibly clinically beneficial interactions of DIM and EGFR inhibitors.

Leiomyoma tissue will be obtained at the time of surgery from women consenting to be donors of their myoma tissue following hysterectomy or myomectomy utilizing the Institutional Review Board. Fresh samples of leiomyoma tissue will be initiated in organ culture following established protocols in the laboratories of Rational Therapeutics, Long Beach, Calif. Published techniques of tissue culture for normal uterine myometrium and leiomyoma tissue include those described by Horiuchi et al. (Horiuchi et al., 2000, Mol Hum Reprod. 6:523-8), and Arici et al. (Arici et al., 2003, Am J Obstet Gynecol. 188(1):76-83). Culture conditions will include the following:

- myoma tissue plus estrogen
- myoma tissue plus estrogen and progesterone
- myoma tissue, estrogen, progesterone, and DIM
- myoma tissue, estrogen, progesterone, and Iressa
- myoma tissue, estrogen, progesterone, DIM and Gefitinib (Iressa, AstraZeneca, UK)
- myoma tissue, estrogen, progesterone, DIM and CI 1033 [Parke-Davis Pharmaceutical Research (Ann Arbor, Mich.)]
- myoma tissue, estrogen, progesterone, DIM and PKI 166 [Novartis Pharma, AG (Basel, Switzerland)]
- myoma tissue, estrogen, progesterone, DIM and Silibinin (LKT Labs, St. Paul, Minn.)
- myoma tissue, estrogen, progesterone, DIM and EGCG (LKT Labs, St. Paul, Minn.)
- myoma tissue, estrogen, progesterone, DIM and Evodiamine (Sigma, St. Louis, Mo.)

Cultures will be subjected to the standardized EVA cell death assay performed by Rational Therapeutics and scored according to rates of apoptosis. The supernatant samples will be frozen and subsequently tested at the Bradlow/Sepkovic Laboratory, Hackensack University Medical Center, Hackensack, N.J. for estrogen metabolites. The method of analysis for supernatants will utilize an established gas chromatography-mass spectrometry (GCMS) assay for the levels of 2-hydroxy, 16-hydroxy, and 4-hydroxy estrone in ng/ml of supernatant (Xu et al., 2002, J Chromatogr B Analyt Technol Biomed Life Sci. 780:315-30).

14. EXAMPLE 9

In Vivo Experiment in Japanese Quail to Demonstrate Prevention of Leiomyomas Using Dim Introduction:

The animal model of monitored growth of the Japanese quail (*Coturnix coturnix japonica*) will be used to demonstrate the utility of DIM, or a DIM-related indole, for the prevention and treatment of spontaneous leiomyomas. Similar to leiomyomas in humans, smooth muscle tumors of the oviduct and the ligament of the oviduct are among the most common benign tumors seen in avian species (Foster et al., 1989, Poult Sci. 68:1447-53). The purpose of this experiment is to demonstrate anti-leiomyoma activity of DIM-related indoles in Japanese quail that is amplified by combined treatment with EGFR inhibitors and/or carotenoid antioxidants. The results are directly applicable to humans and a variety of economically important species of birds.

Methods:

Experimental methods for maintenance of quail, feeding, assessment and sampling of oviduct tissue follow published techniques (Sahin et al., 2004, Nutr Cancer. 50:181-9). 200-300 6-month old Japanese quail (*Coturnix coturnix japonica*) will be used in the study. Groups of 30-40 birds will be assigned to the following Experimental Groups:

1. Control Group: Basal Diet (17% crude protein and 12.4 mJ/kg metabolizable energy)
2. Low Dose DIM Group: Basal Diet plus Formulated DIM (DIM formulated as in Example 1)
3. High Dose DIM Group: Basal Diet plus Formulated DIM
4. Low Dose DIM plus Lycopene: Basal Diet plus Formulated DIM plus Lycopene
5. Low Dose DIM plus Silibinin: Basal Diet plus Formulated DIM plus Silibinin
6. Low Dose DIM plus Evodiamine: Basal Diet plus Formulated DIM plus Evodiamine Birds will receive supplemented diet according to the following dose ranges.

TABLE 9

| Experimental Group | Number (n) | DIM (mg/kg/diet) Low Dose | DIM (mg/kg/diet) High Dose | Lycopene (mg/kg/diet) | Silibinin (mg/kg/diet) | Evodiamine (mg/kg/diet) |
|---|---|---|---|---|---|---|
| Control | (30-40) | | | | | |
| DIM only (Low Dose) | (30-40) | (25-50) | | | | |
| DIM only (High Dose) | (30-40) | | (100-200) | | | |
| DIM and Lycopene | (30-40) | (25-50) | | (100-200) | | |
| DIM and Silibinin | (30-40) | (25-50) | | | (100-300) | |
| DIM and Evodiamine | (30-40) | (25-50) | | | | (25-100) |

At the end of 270-300 days of treatment, birds will be slaughtered and the presence or absence and diameter of leiomyomas in the smooth muscle of the oviduct will be recorded. The tumorous and surrounding normal smooth muscle tissue will be examined histologically. The presence and appearance of leiomyomas will be compared among groups. The tumorous and surrounding normal smooth muscle will be stained using immuno-histochemistry for the presence and levels of phosphorylated Akt and markers of NF kappa b activation using published techniques (Hapman et al., 2004, J Clin Endocrinol Metab. 89:5683-93).

Expected Results:

Fewer and smaller leiomyomas are expected to be found in DIM and DIM plus EGFR inhibitor treated groups of quail. Reduced levels of phosphorylated Akt and markers of NF kappa b activation will be found in smooth muscle and leiomyomas of treated versus control birds.

Discussion

Leiomyomas of the uterus represent a major health problem in the developed world and interfere with reproduction and egg laying in commercial avian species. Treatment with DIM-related indoles, with or without EGFR and/or carotenoid antioxidants, provides a new approach to prevention and non-surgical treatment of leiomyomas and related, benign smooth muscle tumors.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entirety.

What is claimed is:

1. A method of treating leiomyoma in a human having leiomyoma comprising administering to the subject an amount of 3,3' diindolylmethane (DIM) or a DIM-related indole effective to reduce one or more symptoms associated with leiomyoma.

2. The method of claim 1, wherein DIM is administered.

3. The method of claim 1, wherein the DIM-related indole is selected from the group consisting of:

a compound of formula I:

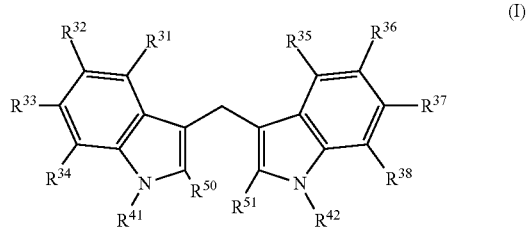

wherein $R^{32}$ and $R^{36}$ are substituents independently selected from the group consisting of hydrogen, hydroxyl, and methoxy, and ethoxycarbonyl groups, $R^{33}$ and $R^{37}$ are substituents independently selected from the group consisting of hydrogen, hydroxyl, and methoxy, $R^{31}$, $R^{34}$, $R^{35}$, $R^{38}$, $R^{41}$, and $R^{42}$ are hydrogen, and $R^{50}$, $R^{51}$ are either hydrogen or methyl;

a compound of formula II:

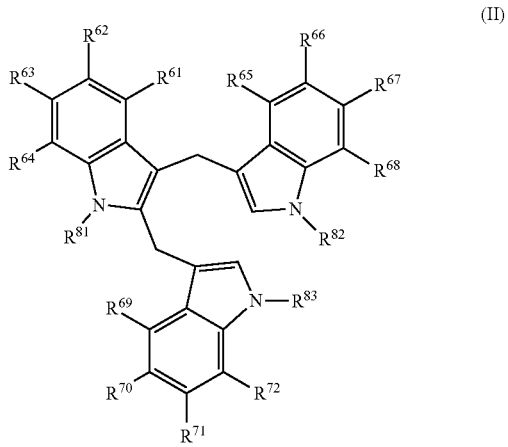

wherein $R^{62}$, $R^{63}$, $R^{66}$, $R^{67}$, $R^{70}$, and $R^{71}$ are substituents independently selected from the group consisting of hydrogen, hydroxyl, and methoxy, and $R^{61}$, $R^{64}$, $R^{65}$, $R^{68}$, $R^{69}$, $R^{72}$, $R^{81}$, $R^{82}$, and $R^{83}$ are hydrogen;

a compound of formula (III):

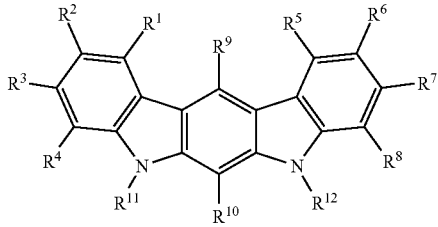

wherein $R^1$, $R^2$, $R^3$, $R^4$, $R^5$, $R^6$, $R^7$, $R^8$, $R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl) amino-substituted $C_1$-$C_{24}$ alkyl, with the provisos that at least one of $R^1$, $R^2$, $R^3$, $R^4$, $R^5$, $R^6$, $R^7$, $R^8$, $R^9$, $R^{10}$, $R^{11}$ and $R^{12}$ is other than hydrogen, and when $R^1$, $R^2$, $R^3$, $R^4$, $R^5$, $R^6$, $R^7$, and $R^8$ are selected from hydrogen, halo, alkyl and alkoxy, then $R^{11}$ and $R^{12}$ are other than hydrogen and alkyl;

a compound of formula (IV):

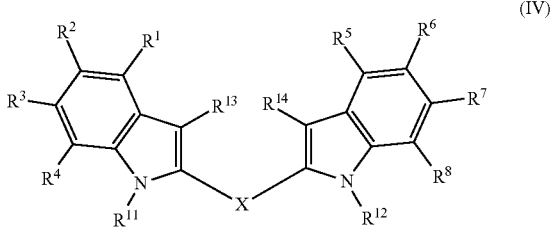

wherein $R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl) amino-substituted $C_1$-$C_{24}$ alkyl, $R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen, and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$; and a compound of formula (V):

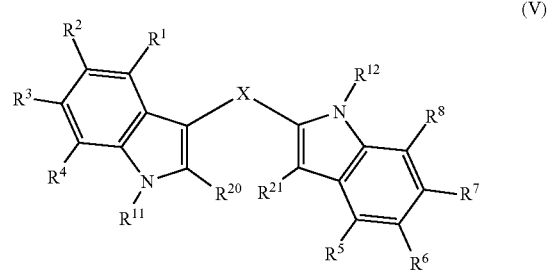

wherein $R^1$, $R^2$, $R^3$, $R^4$, $R^5$, $R^6$, $R^7$, $R^8$, $R^{11}$, $R^{12}$, and X are defined as for compounds of formula (III), and $R^{20}$ and $R^{21}$ are defined as for $R^1$, $R^2$, $R^3$, $R^4$, $R^5$, $R^6$, $R^7$, and $R^8$.

4. The method of claim 1, wherein the DIM-related indole is selected from the group consisting of hydroxylated DIMs, methoxylated DIMs, 2-(Indol-3-ylmethyl)-5 3,3'-diindolylmethane (LTR), hydroxylated LTRs, methoxylated LTRs, 5,5'-dimethylDIM (5-Me-DIM), 2,2'-dimethylDIM (2-Me- DIM), 5,5'-dichloroDIM (5-CI-DIM), imidazolelyl-3,3'-diindolylmethane, nitro-substituted imidazolelyl-3,3'-diindolylmethanes, 2,10-dicarbethoxy-6-methoxy-5,7-dihydroindolo-[2,3-b]carbazole, 6-ethoxycarbonyloxy-5,7-dihydroindolo-[2,3-b]carbazole and 2,10-dicarbethoxy-6-ethoxycarbonyloxy-5,7-dihydro-10 indolo-[2,3-b]carbazole, and 2,6-dicarbethoxy-3,3'-dimethyl-13,14-diindolylmethane.

5. The method of claim 1, wherein the DIM or DIM-related indole is suspended as microparticles in a starch carrier matrix.

6. The method of claim 1, wherein the DIM or DIM-related indole is administered orally.

7. The method of claim 1, wherein the DIM or DIM-related indole is administered intra-arterially.

8. The method of claim 1, wherein the DIM or DIM-related indole is administered vaginally.

9. The method of claim 1, wherein the DIM or DIM-related indole is injected directly into myoma tissue.

10. The method of claim 1, wherein the leiomyoma is an uterine leiomyoma.

11. The method of claim 1, wherein the leiomyoma is an extra-uterine leiomyoma.

12. The method of claim 1, further comprising administering an EGFR antagonist.

13. The method of claim 12, wherein the EGFR antagonist is gefitinib.

14. The method of claim 12, wherein the EGFR antagonist is silibinin, (−)-epigallocatechin-3-gallate, or resveratrol.

* * * * *